(12) United States Patent
Vvedenskiy et al.

(10) Patent No.: US 9,443,302 B2
(45) Date of Patent: Sep. 13, 2016

(54) METHOD AND SYSTEM FOR ROENTGENOGRAPHY-BASED MODELING

(75) Inventors: Petr Stanislavovich Vvedenskiy, Nizhnii Novgorod (RU); Konstantin Evgenevich Mikheev, Sarov (RU); Dmitry Alexandrovich Sivachev, Sarov (RU); Alexander Alexandrovich Morenko, Sarov (RU); Alexander Cherkashin, Flower Mound, TX (US); Mikhail Samchukov, Coppell, TX (US)

(73) Assignees: AMEI TECHNOLOGIES, INC., Wilmington, DE (US); TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 722 days.

(21) Appl. No.: 13/817,778

(22) PCT Filed: Aug. 20, 2010

(86) PCT No.: PCT/RU2010/000452
§ 371 (c)(1),
(2), (4) Date: Apr. 26, 2013

(87) PCT Pub. No.: WO2012/023876
PCT Pub. Date: Feb. 23, 2012

(65) Prior Publication Data
US 2013/0215114 A1 Aug. 22, 2013

(51) Int. Cl.
*G06T 7/00* (2006.01)
*A61B 6/00* (2006.01)

(52) U.S. Cl.
CPC ............ *G06T 7/0012* (2013.01); *A61B 6/584* (2013.01); *G06T 7/0067* (2013.01); *G06T 2200/08* (2013.01); *G06T 2207/10116* (2013.01); *G06T 2207/30008* (2013.01); *G06T 2207/30204* (2013.01)

(58) Field of Classification Search
None
See application file for complete search history.

(56) References Cited

U.S. PATENT DOCUMENTS

| 2,238,870 A | 4/1941 | Haynes |
| 2,346,346 A | 4/1944 | Anderson |
| 4,308,863 A | 1/1982 | Fischer |
| 4,365,624 A | 12/1982 | Jaquet |

(Continued)

FOREIGN PATENT DOCUMENTS

| CA | 2633944 A | 7/2007 |
| CA | 2633944 A1 | 7/2007 |

(Continued)

OTHER PUBLICATIONS

International Search Report, PCT/US2009/034413, dated Apr. 15, 2009, 1 page.

(Continued)

*Primary Examiner* — Said Broome
(74) *Attorney, Agent, or Firm* — Baker & McKenzie LLP

(57) ABSTRACT

Modeling an object in 3-D space may be accomplished various embodiments disclosed herein. An exemplary method of creating a 3-D model includes receiving roentgenograms of an object and at least one reference marker. In some embodiments, the roentgenograms may each include an image of at least one object marker. The exemplary method may further include determining 3-D positions of the x-ray source using the images of the at least one reference marker. The location of the 3-D positions of the x-ray source may allow a 3-D model of the imaged object to be created.

41 Claims, 24 Drawing Sheets

(56) References Cited

U.S. PATENT DOCUMENTS

| | | | |
|---|---|---|---|
| 4,621,627 A | 11/1986 | DeBastiani et al. |
| 4,768,524 A | 9/1988 | Hardy |
| 4,889,111 A | 12/1989 | Ben-Dov |
| 4,973,331 A | 11/1990 | Pursley et al. |
| 4,988,244 A | 1/1991 | Sheldon et al. |
| 5,019,077 A | 5/1991 | De Bastiani et al. |
| 5,095,919 A | 3/1992 | Monticelli et al. |
| 5,156,605 A | 10/1992 | Pursley et al. |
| 5,180,380 A | 1/1993 | Pursley et al. |
| 5,458,599 A | 10/1995 | Adobbati |
| 5,533,418 A | 7/1996 | Wu et al. |
| 5,702,389 A | 12/1997 | Taylor et al. |
| 5,728,095 A | 3/1998 | Taylor et al. |
| 5,776,132 A | 7/1998 | Blyakher |
| 5,863,292 A | 1/1999 | Tosic |
| 5,885,283 A | 3/1999 | Gittleman |
| 5,891,143 A | 4/1999 | Taylor et al. |
| 5,928,230 A | 7/1999 | Tosic |
| 5,971,984 A | 10/1999 | Taylor et al. |
| 5,997,176 A * | 12/1999 | Fairleigh ............... A61B 6/501 378/195 |
| 6,030,386 A | 2/2000 | Taylor et al. |
| 6,379,041 B1 | 4/2002 | Schuetz et al. |
| 7,103,136 B2 | 9/2006 | Claus et al. |
| 7,117,027 B2 | 10/2006 | Zheng et al. |
| 7,282,052 B2 | 10/2007 | Mullaney |
| 7,319,736 B2 * | 1/2008 | Rotondo ............... A61B 6/4233 378/197 |
| 7,331,711 B2 * | 2/2008 | Sandkamp ........... A61B 6/4441 378/114 |
| RE40,914 E | 9/2009 | Taylor et al. |
| 7,672,709 B2 | 3/2010 | Lavallee et al. |
| 7,756,244 B2 | 7/2010 | Mostafavi |
| 8,029,505 B2 | 10/2011 | Hearn et al. |
| 8,104,958 B2 | 1/2012 | Weiser et al. |
| 8,165,659 B2 | 4/2012 | Sheffer et al. |
| 8,202,273 B2 | 6/2012 | Karidis |
| 8,257,353 B2 | 9/2012 | Wong |
| 8,296,094 B2 | 10/2012 | Harrison et al. |
| 8,333,766 B2 | 12/2012 | Edelhauser et al. |
| 8,366,710 B2 | 2/2013 | Hirata et al. |
| 8,377,060 B2 | 2/2013 | Vasta et al. |
| 8,388,619 B2 | 3/2013 | Mullaney |
| 2002/0010465 A1 | 1/2002 | Koo et al. |
| 2003/0139663 A1 | 7/2003 | Graumann |
| 2003/0149378 A1 | 8/2003 | Peabody et al. |
| 2003/0191466 A1 | 10/2003 | Austin et al. |
| 2003/0199856 A1 | 10/2003 | Hill et al. |
| 2003/0212398 A1 | 11/2003 | Jackson |
| 2004/0073211 A1 | 4/2004 | Austin et al. |
| 2004/0097922 A1 | 5/2004 | Mullaney |
| 2004/0116926 A1 | 6/2004 | Venturini et al. |
| 2005/0192572 A1 | 9/2005 | Abdelgany et al. |
| 2005/0215997 A1 | 9/2005 | Austin et al. |
| 2005/0234457 A1 | 10/2005 | James et al. |
| 2006/0052782 A1 | 3/2006 | Morgan et al. |
| 2006/0207118 A1 | 9/2006 | Kim |
| 2006/0235389 A1 | 10/2006 | Albert et al. |
| 2007/0055234 A1 | 3/2007 | McGrath et al. |
| 2007/0055254 A1 | 3/2007 | Ihde |
| 2007/0083087 A1 | 4/2007 | Carda |
| 2007/0085496 A1 | 4/2007 | Philipp et al. |
| 2007/0211849 A1 | 9/2007 | Movassaghi et al. |
| 2007/0225704 A1 | 9/2007 | Ziran et al. |
| 2007/0233134 A1 | 10/2007 | Bastian et al. |
| 2008/0021451 A1 | 1/2008 | Coull et al. |
| 2009/0036890 A1 | 2/2009 | Karidis |
| 2009/0036892 A1 | 2/2009 | Karidis et al. |
| 2010/0087819 A1 | 4/2010 | Mullaney |
| 2010/0262160 A1 | 10/2010 | Boyden et al. |
| 2010/0262239 A1 | 10/2010 | Boyden et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0004199 A1 | 1/2011 | Ross et al. |
| 2011/0071389 A1 | 3/2011 | Simon et al. |
| 2011/0103676 A1 | 5/2011 | Mullaney |
| 2011/0118738 A1 | 5/2011 | Vasta et al. |
| 2011/0166572 A1 | 7/2011 | Ihde |
| 2011/0262024 A1 | 10/2011 | Bulitta et al. |
| 2011/0313418 A1 | 12/2011 | Nikonovas |
| 2011/0313419 A1 | 12/2011 | Mullaney |
| 2012/0041439 A1 | 2/2012 | Singh et al. |
| 2012/0130384 A1 | 5/2012 | Henderson |
| 2012/0303028 A1 | 11/2012 | Wong |
| 2012/0303029 A1 | 11/2012 | Vasta et al. |
| 2013/0018374 A1 | 1/2013 | Edelhauser et al. |

FOREIGN PATENT DOCUMENTS

| | | | |
|---|---|---|---|
| DE | 3802743 A1 | 8/1989 |
| DE | 9316164 U1 | 7/1994 |
| DE | 4421223 A1 | 12/1995 |
| DE | 102007026404 A1 | 12/2008 |
| EP | 0029298 A | 5/1981 |
| EP | 1239784 B1 | 4/2006 |
| EP | 1916952 B1 | 12/2009 |
| EP | 2134515 B1 | 7/2010 |
| EP | 2417923 A1 | 2/2012 |
| GB | 421788 | 12/1934 |
| GB | 2229096 A | 9/1990 |
| IT | 1259768 B | 3/1996 |
| JP | S52-003290 | 8/1978 |
| JP | S63-500499 | 2/1988 |
| JP | H02180254 A | 7/1990 |
| JP | H10290807 A | 11/1998 |
| JP | 2003508108 A | 3/2003 |
| JP | 2003508150 A | 3/2003 |
| JP | 2005-137586 | 6/2005 |
| WO | 9222268 A1 | 12/1992 |
| WO | 9626678 A1 | 9/1996 |
| WO | 9730650 A1 | 8/1997 |
| WO | 9812975 A2 | 4/1998 |
| WO | 9815231 A1 | 4/1998 |
| WO | 9920193 A1 | 4/1999 |
| WO | 9947060 A1 | 9/1999 |
| WO | 9948414 A2 | 9/1999 |
| WO | 0003647 A1 | 1/2000 |
| WO | 0115611 A1 | 3/2001 |
| WO | 0122892 A1 | 4/2001 |
| WO | 03086211 A1 | 10/2003 |
| WO | 03086212 A2 | 10/2003 |
| WO | 03086213 A2 | 10/2003 |
| WO | 2004026103 A2 | 4/2004 |
| WO | 2007002180 A2 | 1/2007 |
| WO | 2007060507 A2 | 5/2007 |
| WO | 2007139031 A1 | 12/2007 |
| WO | 2008002992 A1 | 1/2008 |
| WO | 2008134624 A1 | 11/2008 |
| WO | 2009018349 A2 | 2/2009 |
| WO | 2009018398 A2 | 2/2009 |
| WO | 2009100247 A1 | 8/2009 |
| WO | 2009100459 A1 | 8/2009 |
| WO | 2009102904 A1 | 8/2009 |
| WO | 2009105479 A1 | 8/2009 |
| WO | 2010042619 A1 | 4/2010 |
| WO | 2010104567 A1 | 9/2010 |
| WO | 2010120367 A1 | 10/2010 |
| WO | 2011017321 A2 | 2/2011 |
| WO | 2011060264 A1 | 5/2011 |
| WO | 2011060266 A1 | 5/2011 |
| WO | 2011106507 A1 | 9/2011 |
| WO | 2011146703 A1 | 11/2011 |
| WO | 2011163406 A2 | 12/2011 |

OTHER PUBLICATIONS

International Preliminary Report on Patentability, PCT/US2009/034413, dated Aug. 24, 2010, 7 pages.

Extended European Search Report, Application No. 09712412.7-1526, PCT/US2009/034413, dated Dec. 3, 2012, 10 pages.

International Search Report, PCT/US2010/056541, dated Jan. 12, 2011, 1 page.

(56) References Cited

OTHER PUBLICATIONS

International Preliminary Report on Patentability, PCT/US2010/056541, Date of issuance May 15, 2012, 7 pages.
International Preliminary Report on Patentability, PCT/US2010/056539, Date of issuance May 15, 2012, 9 pages.
International Search Report, PCT/US2010/056539, Dated Jan. 18, 2011, 2 pages.
Steffen Schumann, et al., "Calibration of X-ray radiographs and its feasible application for 2D/3D reconstruction of the proximal femur" (2008), 4 pages.
Jetzki S., et al., "Fluoroscopy-Based 3-D Reconstruction of Femoral Bone Cement: A New Approach for Revision Total Hip Replacement," (2005), 12 pages.
Guoyan Zheng, et al., "3-D reconstruction of a surface model of the proximal femur from digital biplanar radiographs," (2008), 4 pages.
Laporte S., et al., "A biplanar reconstruction method based on 2D and 3D contours: application to the distal femur," (2003), 6 pages.
Japanese Office Action, JP Application No. 2010-546960, dated Mar. 12, 2013, 4 pages.
Japanese Office Action, JP Application No. 2010-546904, dated Mar. 12, 2013, 6 pages.
Japanese Office Action, JP Application No. 2010-546098, dated Mar. 5, 2013, 11 pages.
International Preliminary Report on Patentability, PCT/RU2010/000452, dated Feb. 26, 2013, 9 pages.
Japanese Office Action, JP Application No. 2010-545284, dated Mar. 5, 2013, 6 pages.
Japanese Office Action, dated Nov. 26, 2013, JP Application No. 2010-545284, 4 pages.
Japanese office action, JP Application No. 2010-546904, dated Oct. 29, 2013, 4 pages.
European Extended Search Report, EP Application No. 09710983.9-1654 / 2249721 PCT/US2009/033975, dated Apr. 4, 2014, 7 pages.
European Extended Search Report, Application No. 09707791.1-1654 / 2240084, PCT/US2009/033258, dated Nov. 21, 2013, 6 pages.
International Search Report and Written Opinion, PCT/US2013/064067, dated Jan. 31, 2014, 7 pages.
International Search Report and Written Opinion, PCT/RU2013/000203, dated Jan. 29, 2014, 23 pages.
Canero, C., et al., "Predictive (Un)distortion Model and 3-D Reconstruction by Biplane Snakes, IEEE Transactions on Medical Imaging," vol. 21, No. 9, (Sep. 2002), 14 pages.
Ghanem, R.N., et al., "Heart-Surface Reconstruction and ECG Electrodes Localization Using Fluoroscopy, Epipolar Geometry and Stereovision: Application to Noninvasive Imaging of Cardiac Electrical Activity," IEEE Transactions on Medical Imaging, vol. 22, No. 10, (Oct. 2003), 12 pages.
Li, Y., et al., "Distortion Correction and Geometric Calibration for X-Ray Angiography System," IEEE Transactions on Nuclear Science, vol. 56, No. 3, (Jun. 2009), 12 pages.
Selby, B.P., et al., "Patient positioning with X-ray detector self-calibration for image guided therapy," Australas Phys. Eng. Sci. Med., vol. 34, (2011), 10 pages.
Yang, J., et al., "Novel Approach for 3-D Reconstruction of Coronary Arteries From Two Uncalibrated Angiographic Images," IEEE Transactions on Image Processing, vol. 18, No. 7, (Jul. 2009), 10 pages.
Zheng, G., et al., "A 2D/3D correspondence building method for reconstruction of a patient-specific 3D bone surface model using point distribution models and calibrated X-ray images," Medical Image Analysis, vol. 13, (2009), 17 pages.
Extended European Search Report, EP 09708841.3-1654 / 2240085; PCT/US2009/033603, dated Dec. 2, 2013, 5 pages.

\* cited by examiner

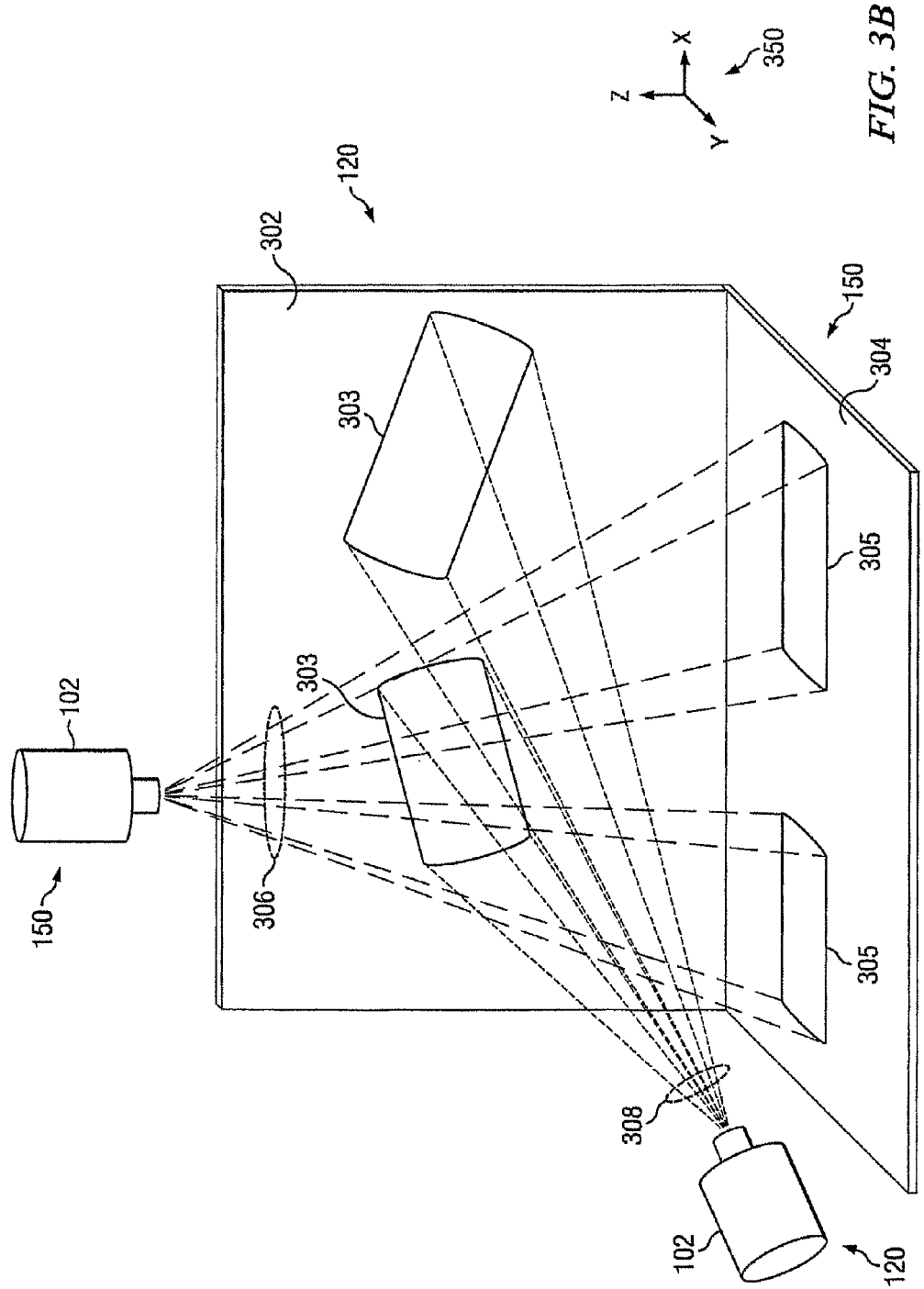

METHOD AND SYSTEM FOR ROENTGENOGRAPHY-BASED MODELING

TECHNICAL FIELD

The present disclosure relates in general to the field of roentgenography, and more specifically, to creating three-dimensional (3-D) models of objects in space based on two-dimensional (2-D) roentgenograms.

BACKGROUND

Modeling an object in 3-D space has a number of useful applications. A 3-D model of objects may allow one to more easily visualize and analyze orientations of the objects relative to each other. This aspect of modeling is particularly useful in orthopedics, or more specifically, in analyzing bone deformities. Computed tomography (CT) is one conventional technique that has been used in the field of orthopedics to generate 3-D representation of human tissues. Another conventional technique involves visualizing and analyzing bone deformities with the aid of 2-D roentgenograms. First, radiographic images of deformed bone segments are obtained in orthogonal views. Subsequently, the deformities can be analyzed by creating 2-D linear representations of the imaged bone segments and projecting such linear representations in the plane of the deformity. Alternatively, the outlines of the deformed bone segments in the 2-D roentgenograms may be manually determined and extrapolated to build a 3-D model of the deformed bone segments.

SUMMARY

The present disclosure provides a method of creating a 3-D model of an object. In an embodiment, the method comprises: 1) receiving a first roentgenogram of an object disposed between an x-ray source and an x-ray imager in a first orientation, wherein the first orientation comprises a first angular position of the object relative to an imaging axis, wherein the first roentgenogram includes a first image of the object and at least one reference marker having at least two fiducials, wherein the fiducials are separated by a fixed distance; 2) receiving a second roentgenogram of the object disposed between the x-ray source and the x-ray imager in a second orientation, wherein the second orientation comprises a second angular position of the object relative to the imaging axis, and wherein the second roentgenogram includes a second image of the object and the at least one reference marker; 3) receiving an angular displacement corresponding to the difference between the first and second angular positions of the object relative to the imaging axis; 4) determining a first 3-D position of the x-ray source with respect to the x-ray imager in the first orientation using the first image of the at least one reference marker; 5) determining a second 3-D position of the x-ray source with respect to the x-ray imager in the second orientation using the second image of the at least one reference marker; 6) identifying a first object outline of the imaged object in the first roentgenogram; 7) identifying a second object outline of the imaged object in the second roentgenogram; 8) preparing a first 3-D object projection from the first outline of the imaged object to the first 3-D position of the x-ray source; 9) preparing a second 3-D object projection from the second outline of the imaged object to the second 3-D position of the x-ray source; 10) aligning the first and second 3-D projections of the imaged object in a 3-D reference frame using the angular displacement; and 11) creating a 3-D model of the imaged object in the 3-D reference frame based on the first and second 3-D object projections. In any of the embodiments disclosed herein, the method of creating a 3-D model of an object may further include: 1) identifying a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation; 2) identifying one or more intersection planes passing through the tilt axis and through the first and second 3-D projections of the imaged object in the 3-D reference frame; 3) for each of the one or more intersection planes, performing the following steps: a) identifying one or more intersection points between the first and second 3-D object projections, and said intersection plane in the 3-D reference frame; b) preparing one or more polygons connecting the intersection points in said intersection plane; c) preparing one or more closed curves within the each of the one or more polygons, wherein the one or more closed curves corresponds to a cross-sectional view of the imaged object in said intersection plane; and 4) preparing a surface in the 3-D reference frame that connects each of the closed curves to form a 3-D model of the imaged object. Furthermore, in any of the applicable embodiments disclosed herein, the at least one reference marker may comprise at least three fiducials in total, and the method may further comprise receiving a first outline of the at least three fiducials in the first roentgenogram and receiving a second outline of the at least three fiducials in the second roentgenogram; wherein the determining the first 3-D position of the x-ray source comprises identifying a first plurality of paths from the x-ray source to the first outline of the at least three fiducials and determining an approximate intersection of the first plurality of paths; and wherein the determining the second 3-D position of the x-ray source comprises identifying a second plurality of paths from the x-ray source to the first outline of the at least three fiducials and determining an approximate intersection of the second plurality of paths. In some embodiments, the determining the approximate intersection of the first plurality of paths and the approximate intersection of the second plurality of paths may comprise using an approximation model in accordance with the present disclosure.

Another method of creating a 3-D model of an object may comprise: 1) receiving a first roentgenogram of an object disposed between an x-ray source and an x-ray imager in a first orientation, wherein the first orientation comprises a first angular position of the object with respect to an imaging axis, wherein the imaging axis is parallel to the imager in the first orientation, wherein the first roentgenogram includes a first image of the object and at least one reference marker having at least two fiducials, wherein the fiducials are separated by a fixed distance; 2) receiving a second roentgenogram of the object disposed between the x-ray source and the x-ray imager in a second orientation, wherein the second orientation comprises a second angular position of the object with respect to the imaging axis, wherein the imaging axis is parallel to the imager in the second orientation and the second angular position of the object is substantially orthogonal to the first angular position of the object, and further wherein the second roentgenogram includes a second image of the object and the at least one reference marker; 3) determining a first 3-D position of the x-ray source with respect to the x-ray imager in the first orientation using the first image of the at least one reference marker; 4) determining a second 3-D position of the x-ray source with respect to the x-ray imager in the second orientation using the second image of the at least one reference marker; 5) identifying a first object outline of the imaged object in the first roentgenogram; 6) identifying a second object outline of the imaged object in the second roentgenogram; 7) preparing a first 3-D object projection from the first outline of the imaged object to the first 3-D position of the x-ray source; 8) preparing a second 3-D object projection from the second outline of the imaged object to the second 3-D position of the x-ray source; 9) aligning the first and second 3-D projections of the imaged object in a 3-D reference frame according to the substantially orthogonal first and second angular positions of the object; and 10) creating a 3-D model of the imaged object in the 3-D reference frame based on the first and second 3-D object projections.

Another embodiment of a method of creating a 3-D model of an object may include: 1) receiving a first roentgenogram of an object disposed between an x-ray source and an x-ray imager in a first orientation, wherein the first orientation comprises a first angular position of the object relative to an imaging axis, wherein the first roentgenogram includes a first image of the object at least one reference marker having at least two fiducials, wherein the fiducials are separated by a fixed distance, and at least one object marker attached to the object, wherein the object marker includes at least one fiducial of fixed dimensions; 2) receiving a second roentgenogram of the object disposed between the x-ray source and the x-ray imager in a second orientation, wherein the second orientation comprises a second angular position of the object relative to the imaging axis, and wherein the second roentgenogram includes a second image of the object the at least one reference marker, and the at least one object marker; 3) determining a first 3-D position of the x-ray source with respect to the x-ray imager in the first orientation using the first image of the at least one reference marker; 4) determining a second 3-D position of the x-ray source with respect to the x-ray imager in the second orientation using the second image of the at least one reference marker; 5) identifying a first object outline of the imaged object in the first roentgenogram; 6) identifying a second object outline of the imaged object in the second roentgenogram; 7) preparing a first 3-D object projection from the first object outline to the first 3-D position of the x-ray source; 8) preparing a first 3-D object marker projection from the object marker in the first roentgenogram to the first 3-D position of the x-ray source; 9) preparing a second 3-D object projection from the second object outline to the second 3-D position of the x-ray source; 10) preparing a second 3-D object marker projection from the object marker in the second roentgenogram to the second 3-D position of the x-ray source; 11) aligning the first and second 3-D object marker projections in a 3-D reference frame using the first and second object marker projections; 12) aligning the first and second 3-D projections of the imaged object in the 3-D reference frame using the alignment of the first and second 3-D object marker projections in the 3-D reference frame; and 13) creating a 3-D model of the imaged object in the 3-D reference frame based on the first and second 3-D object projections.

One exemplary embodiment of a method of creating a 3-D model of an object may include: 1) receiving a first roentgenogram of an object disposed between an x-ray source and an x-ray imager in a first orientation, wherein the first orientation comprises a first angular position of the object relative to an imaging axis, wherein the first roentgenogram includes a first image of the object at least one reference marker having at least two fiducials, wherein the fiducials are separated by a fixed distance, and at least one ring having a fixed diameter, wherein the ring is attached to the object; 2) receiving a second roentgenogram of the object disposed between the x-ray source and the x-ray imager in a second orientation, wherein the second orientation comprises a second angular position of the object relative to the imaging axis, wherein the second roentgenogram includes a second image of the object, the at least one reference marker, and the ring; 3) determining a first 3-D position of the x-ray source with respect to the x-ray imager in the first orientation using the first image of the at least one reference marker; 4) determining a second 3-D position of the x-ray source with respect to the x-ray imager in the second orientation using the second image of the at least one reference marker; 5) receiving a first ring outline of the imaged ring in the first roentgenogram; 6) preparing a first 3-D ring projection from the first ring outline in the first roentgenogram to the first 3-D position of the x-ray source; 7) determining a first ring position from the x-ray imager in the first orientation using the first 3-D ring projection and the fixed diameter of the ring; 8) receiving a second ring outline of the imaged ring in the second roentgenogram; 9) preparing a second 3-D ring projection from the second ring outline in the second roentgenogram to the second 3-D position of the x-ray source; 10) determining a second ring position from the x-ray imager in the second orientation using the second 3-D ring projection and the fixed diameter of the ring; 11) determining the 3-D position of the ring with respect to the x-ray imager in the first and second orientations using the first and second ring outlines and the first and second ring positions; 12) identifying a first object outline of the imaged object in the first roentgenogram; 13) preparing a first 3-D object projection from the first outline of the imaged object to the first 3-D position of the x-ray source; 14) identifying a second object outline of the imaged object in the second roentgenogram; 15) preparing a second 3-D object projection from the second outline of the imaged object to the second 3-D position of the x-ray source; 16) aligning the first and second 3-D object projections in a 3-D reference frame using the 3-D positions of the ring with respect to the x-ray imager in the first and second orientations; and 17) creating a 3-D model of the imaged object in the 3-D reference frame based on the first and second 3-D object projections.

Systems for creating a 3-D model of an object are also disclosed.

BRIEF DESCRIPTION OF THE DRAWINGS

For a more complete understanding of the features and advantages of the present disclosure, reference is now made to the detailed description along with the accompanying figures, in which:

FIG. 3B is a schematic diagram illustrating the orientations of a light source and the corresponding roentgenograms shown in FIG. 3A, in accordance with the present disclosure;

DETAILED DESCRIPTION

Figure 1A:
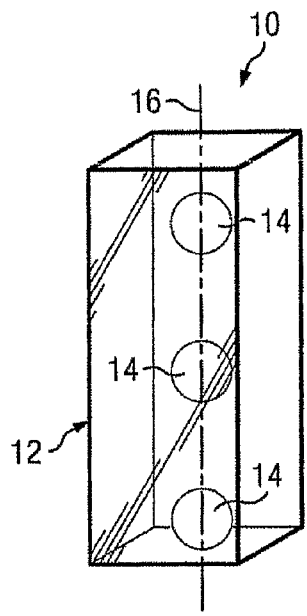
FIG. 1A is a perspective view of a first embodiment of a reference marker, in accordance with the present disclosure.

Conventional techniques for generating 3-D models have many shortcomings. A CT scan generates a set of cross-sectional images that can be combined to produce a 3-D representation of human tissues. The use of CT scans in orthopedic applications, however, may not be practical due to several limitations. During a CT scan, the patient is subject to a relatively large amount of radiation, and repeated use of CT scan can expose the patient to excessive radiation and present health risk. Furthermore, a CT scan is relatively expensive, and is not suitable to image metals, which can cause undesirable distortions. Moreover, the patient is required to remain still during the CT scan, and anesthesia may be required if the patent is a young child. The use of anesthesia, however, increases the cost of treatment and may present additional health risk.

As discussed above, another conventional technique involves manually determining the outlines of the deformed bone segments in 2-D roentgenograms and extrapolating the 2-D outlines to build a 3-D model of the deformed bone segments. A variety of factors, however, can adversely affect the accuracy of the models created using such a technique. First, projecting linear representations of deformed bone segments do not account for the girth of the bone segments in 3-D space and may cause a physician to prescribe treatments that do not sufficiently correct the bone deformities. Moreover, models created by conventional techniques are based on the assumption that roentgenograms were taken at orthogonal positions, and the accuracy of the model is adversely affected when this is not the case. Although a technician can be trained to estimate orthogonal positions for taking the roentgenograms, minor human errors are inevitable and thus render the models generated by conventional techniques inaccurate. Furthermore, due to the magnification effect of x-rays traveling from an x-ray source to an imager, the object in the roentgenograms appears larger than its actual size. To account for the magnification effect, an reference marker(s) of known dimensions has to be precisely disposed on the object proximate to the region of interest, and the known dimensions of the reference marker is used to determine and account for the magnification effect. Again, the inevitable human imprecision in the placement of the reference marker can lead to inaccuracy.

Due to the above described errors in conventional techniques, the linear and angular parameters obtained are projections rather than true parameters. Projections do not correspond to the true size or shape of objects; they are distorted relative to the true shape of the object. Such techniques are not adequate to accurately determine the coordinates of the points on a chosen object in 3-D space, and in orthopedic applications, such methods are not adequate to accurately calculate the desired distraction, compression, displacement, or other movement of tissue segments.

The present disclosure provides techniques for creating a 3-D model of an object using roentgenograms. From the present disclosure, one of ordinary skill in the art will appreciate that the techniques of the present disclosure may obviate the need to use a precisely placed marker to account for the magnification effect of x-rays. The techniques of the present disclosure also may not require roentgenograms taken at orthogonal positions and may be suitable for roentgenograms taken at various relative orientations.

One embodiment of the techniques disclosed herein comprises receiving first and second roentgenograms of an object disposed between an x-ray source and an imager. The first and second roentgenograms depict the object in first and second orientations relative to the x-ray source and the imager, respectively. The first roentgenogram includes a first image of the object and a first image of at least one reference marker. In some embodiments, the first roentgenogram also includes a first image of at least one object marker disposed at a fixed orientation with respect to the object. In some embodiments, however, no object marker is used, and the first roentgenogram would not include an image of an object marker. The second roentgenogram similarly includes a second image of the object and a second image of the at least one reference marker. In some embodiments, the second roentgenogram includes a second image of the at least one object marker. Again, in some embodiment, no object marker is used, and the second roentgenogram would not include an image of an object marker.

Figure 1B:
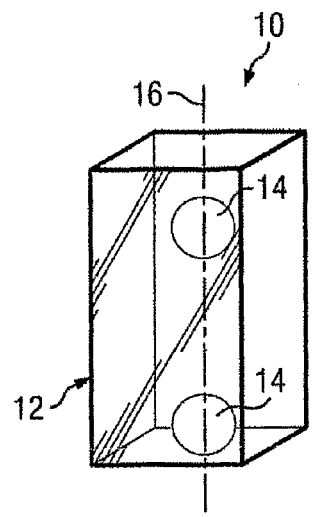
FIG. 1B is a perspective view of a second embodiment of a reference marker, in accordance with the present disclosure.
Figure 1C:
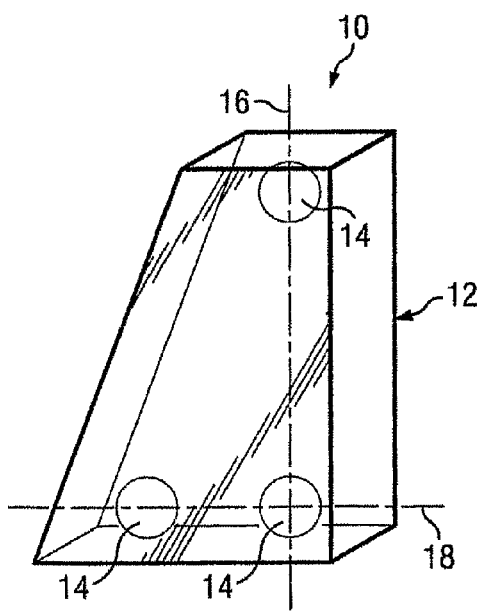
FIG. 1C is a perspective view of a third embodiment of a reference maker, in accordance with the present disclosure.

Shown in FIGS. 1A-C are several exemplary embodiments of the reference markers that are suitable for being imaged in a roentgenogram. The reference marker 10 in FIGS. 1A-C comprises a body 12 and a plurality of fiducials 14 disposed therein. The body 12 is made of a material that is substantially translucent to short-wavelength radiation, such as x-rays, and can have a variety of shapes and dimensions to accommodate for the desired orientations of the fiducials 14. The fiducials 14 are made of a radiographically opaque material such that the fiducials 14 are readily identifiable in a roentgenogram. In an alternative embodiment, the body 12 may be made of a radio-opaque material, and the plurality of fiducials 14 may be a plurality of translucent portions in the body 12. For example, the body 12 may include a plurality of holes defined therethrough. Due to the contrast in radio-opacity, the plurality of holes may be readily identifiable in an x-ray image of the reference marker 10. It is to be appreciated that this configuration may be incorporated in any of the embodiments discussed in the present disclosure.

In some embodiments, it is also desirable to be able to uniquely identify each fiducial 14. Accordingly, the fiducials 14 may each have a different shape, different radiographic opacity, or a different size. Each marker 10 may also comprise a different number of fiducials for identification purpose. For example, a first marker 10 may comprise individual fiducials in pairs, and a second marker 10 may comprise individual fiducials in triplets.

The number and positions of the fiducials 14 in each marker 10 may vary, depending on the design parameters discussed in the present disclosure. In the embodiment shown in FIG. 1A, the marker 10 comprises three fiducials 14 aligned along a longitudinal axis 16. In the embodiment shown in FIG. 1B, the marker 10 comprises only two fiducials 14 aligned along the longitudinal axis 16. In the embodiment shown in FIG. 1C, the marker 10 comprises three fiducials 14 aligned along orthogonal axes 16 and 18. In each of these embodiments, the distances between the fiducials 14 have been predetermined.

Figure 2A:
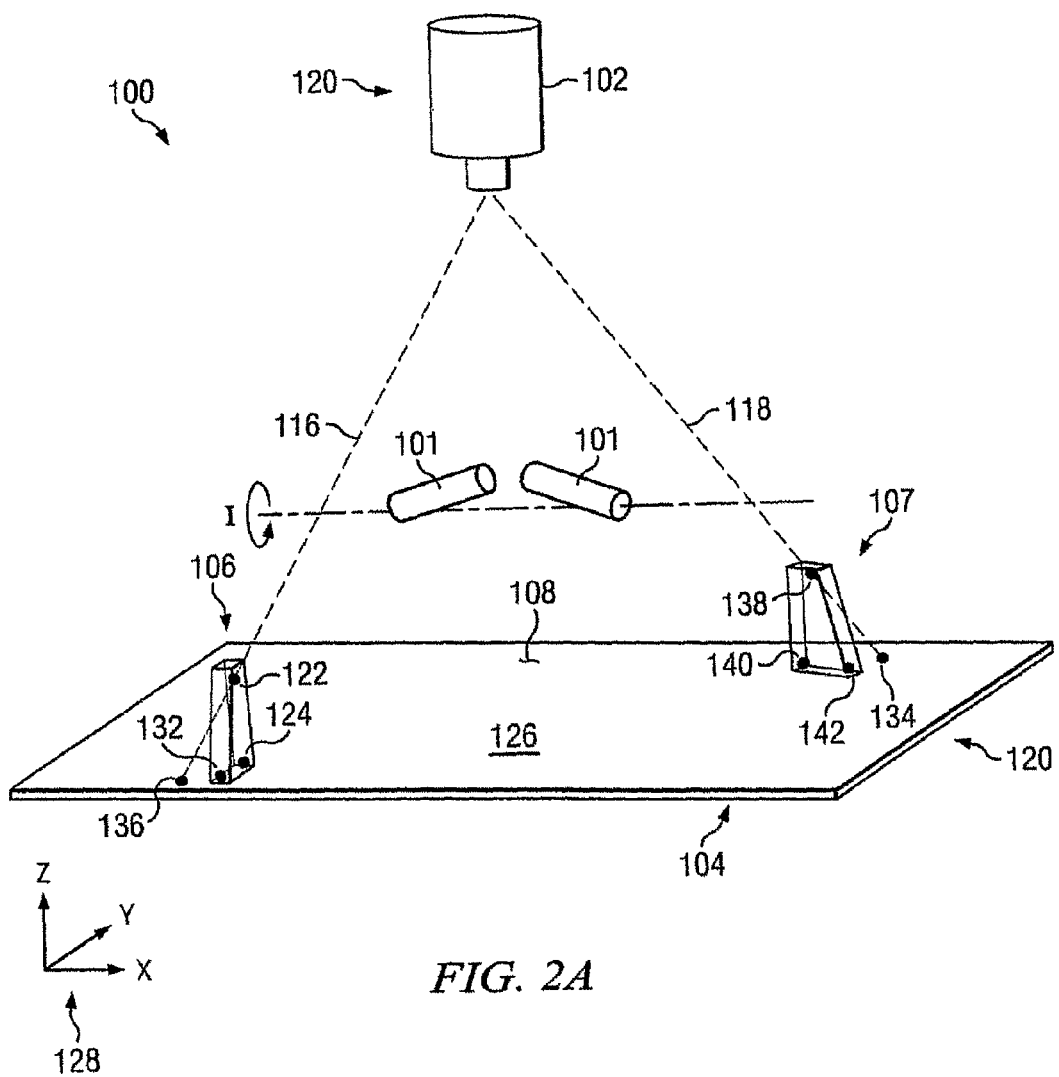
FIG. 2A is a perspective view of an imaging system and an object in a first relative orientation, in accordance with the present disclosure.
Figure 2B:
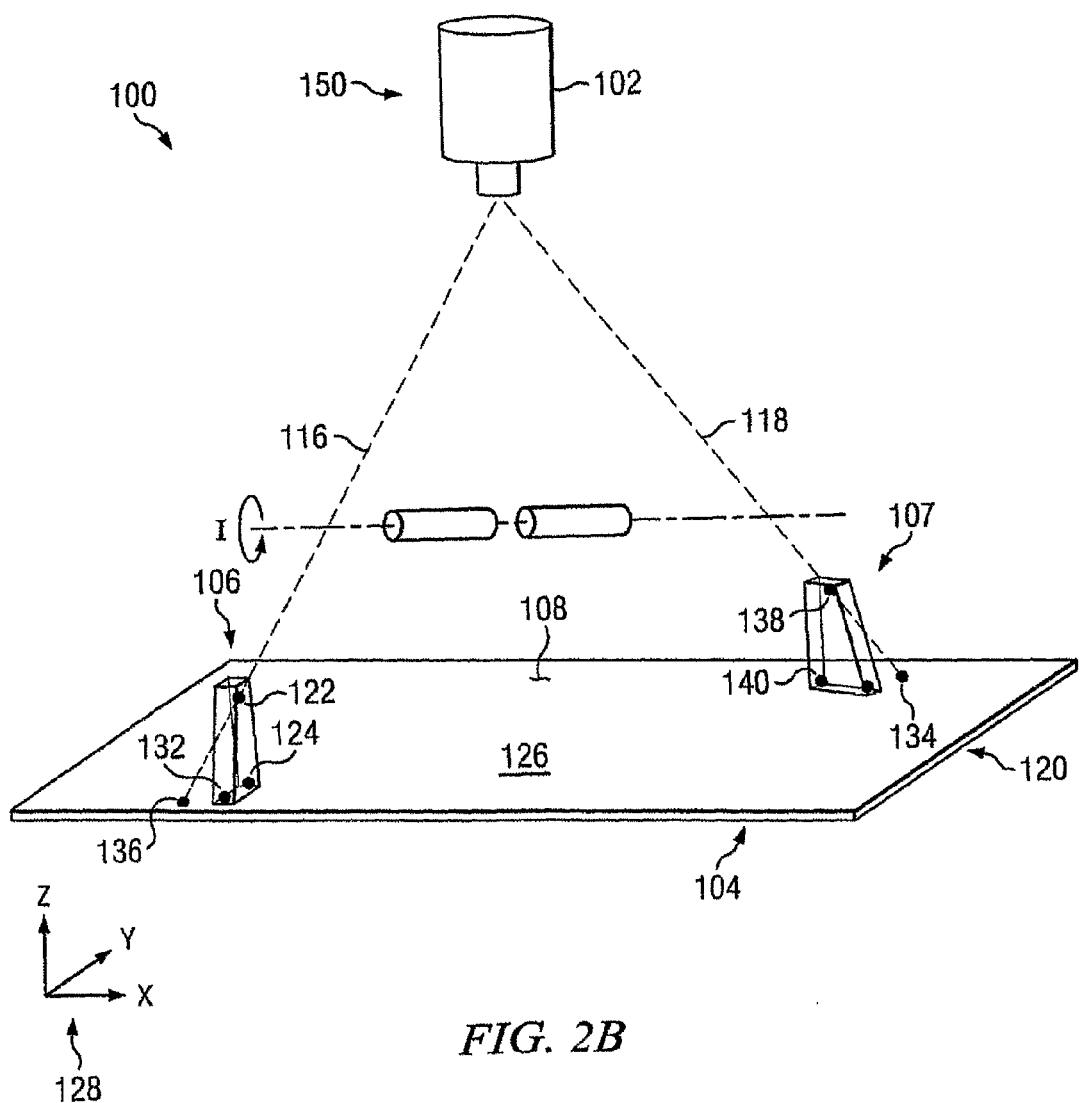
FIG. 2B is a perspective view of the imaging system and the object shown in FIG. 2A in a second relative orientation, in accordance with the present disclosure.

In an embodiment, the marker 10 is mounted on an imager 104, which is described in greater details with respect to FIGS. 2A-B. When the marker 10 is mounted on the imager 104, a first fiducial 14 is proximate to the surface of an imager 104, and the longitudinal axis 16 is orthogonal to the surface of the imager 104. As such, the distance between a second fiducial 14 and the surface of the imager 104 can be determined using the predetermined distances between the first and second fiducials 14. If the marker 10 shown in FIG. 1C is used, the axis 18 is preferably parallel with respect to the surface of the imager 104 for reasons to be discussed below.

A variety of markers 10 may be chosen to be mounted on the imager 104, depending on the number and positions of the fiducials 14 of each marker 10 used or any other design parameters discussed in the present disclosure. The choice and use of the marker 10 is discussed with reference to FIGS. 2A-C. FIG. 2A is a schematic diagram of an imaging system 100 operable to obtain first and second roentgenograms. The imaging system 100 comprises an x-ray source 102, an imager 104, and at least one reference marker 106. The imager 104 comprises an imaging surface 108 wherein the reference marker 106 can be coupled to the imaging surface 108. The reference marker 106 may be configured according to the principles discussed with reference to FIGS. 1A-C.

To obtain the first and second roentgenograms, an object 101 is placed between the x-ray source 102 and the imager 104. To generate the first roentgenogram, the object 101, the x-ray source 102, and the imager 104 are in a first orientation 120 relative to each other. The second roentgenogram may be generated by either rotating the object 101 to a new orientation with respect to the x-ray source 102 and imager 104, or by rotating the x-ray source 102 and imager 104 to a new orientation about the object 101. According to the former method, the object 101 is rotated with respect to the x-ray source 102 and the imager 104, as shown in FIG. 2B, such that the object 101, the x-ray source 102, and the imager 104 are in a second relative orientation 150 relative to each other.

In an embodiment, the object 101 is rotated orthogonally about a first imaging axis I, in which case, the first and second relative orientations 120 and 150 are orthogonal with respect to each other. The orthogonal rotation of the object 101 can be effected with the aid of a device operable to monitor and/or measure the rotational movement of the object 101. In one embodiment, a sensor is directly or indirectly coupled to the object 101 for measuring the angular rotation of the object 101. The sensor may include any suitable device operable to monitor and/or measure angular orientation, such as a level. In an embodiment, the sensor may include an accelerometer configured to provide a signal (e.g. an audible alert) when the object 101 has arrived at a desired orientation relative to the initial orientation. In an embodiment in which an orthogonal rotation is desired, the accelerometer may provide a signal when the orthogonal rotation is effected. The accelerometer may further be operable to provide a signal when the object 101 is unintentionally rotated about axes other than the imaging axis, thereby allowing a technician to avoid the unintentional rotation of the object 101.

Figure 1D:
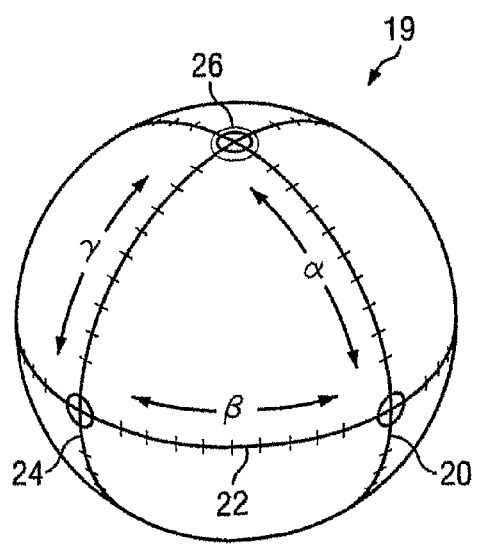
FIG. 1D is a perspective view of an embodiment of a spherical level, in accordance with the present disclosure.

According to another embodiment, the sensor attached to the object may include a "T" level or spherical level so as to monitor the orientation of the object 101 and make any necessary adjustments. A representative example of a spherical level 19 is depicted in FIG. 1D, where the sphere is marked with three separate lines (20, 22, 24) that pass around the diameter of the sphere. Each of the lines bisects the sphere into hemispheres that are orthogonal with respect to each other. Each of the lines is marked with fiducials indicating the angle between the fiducial and a corresponding intersection (e.g., 10 degrees, 20 degrees, etc.). Preferably, the sphere is translucent, so that a bubble 26 or other marker floating inside the sphere can be used to measure the relative orientation of the sphere. The sphere can be releasably mounted to a bracket (not shown), which itself may be affixed to an object, or to a frame mounted to an object. When the object is placed in the first orientation, the level 19 can be initialized to that location by moving the sphere until the bubble 26 or marker is aligned with an intersection of lines on the level 19. Once the bubble 26 or marker is aligned with the intersection, the sphere can be locked with respect to the bracket. After this, the relative orientation of the object 101 can be accurately measured in three dimensions. Thus, the object 101 can be readily moved to a new desired orientation, such as one that is orthogonal to its original orientation.

In an exemplary embodiment, the object 101 is rotated about an imaging axis I such that the first and second relative orientations 120 and 150 are oblique with respect to each other. The angular rotation of the object 101 can be measured with the aid of a sensor operable to monitor and measure the rotational movement of the object 101. The sensor may be further operable to provide a signal when the x-ray source 102 and/or the imager 104 are unintentionally rotated about axes other than the imaging axis I, thereby alarming a technician to correct the unintentional rotational movement. In one embodiment, a sensor is directly or indirectly coupled to the object 101 for measuring the angular rotation of the object 101. In an embodiment, the sensor may include an accelerometer, a calibrated level, or any other suitable device either described in the present disclosure or known in the art for measuring angular rotations.

Figure 2C:
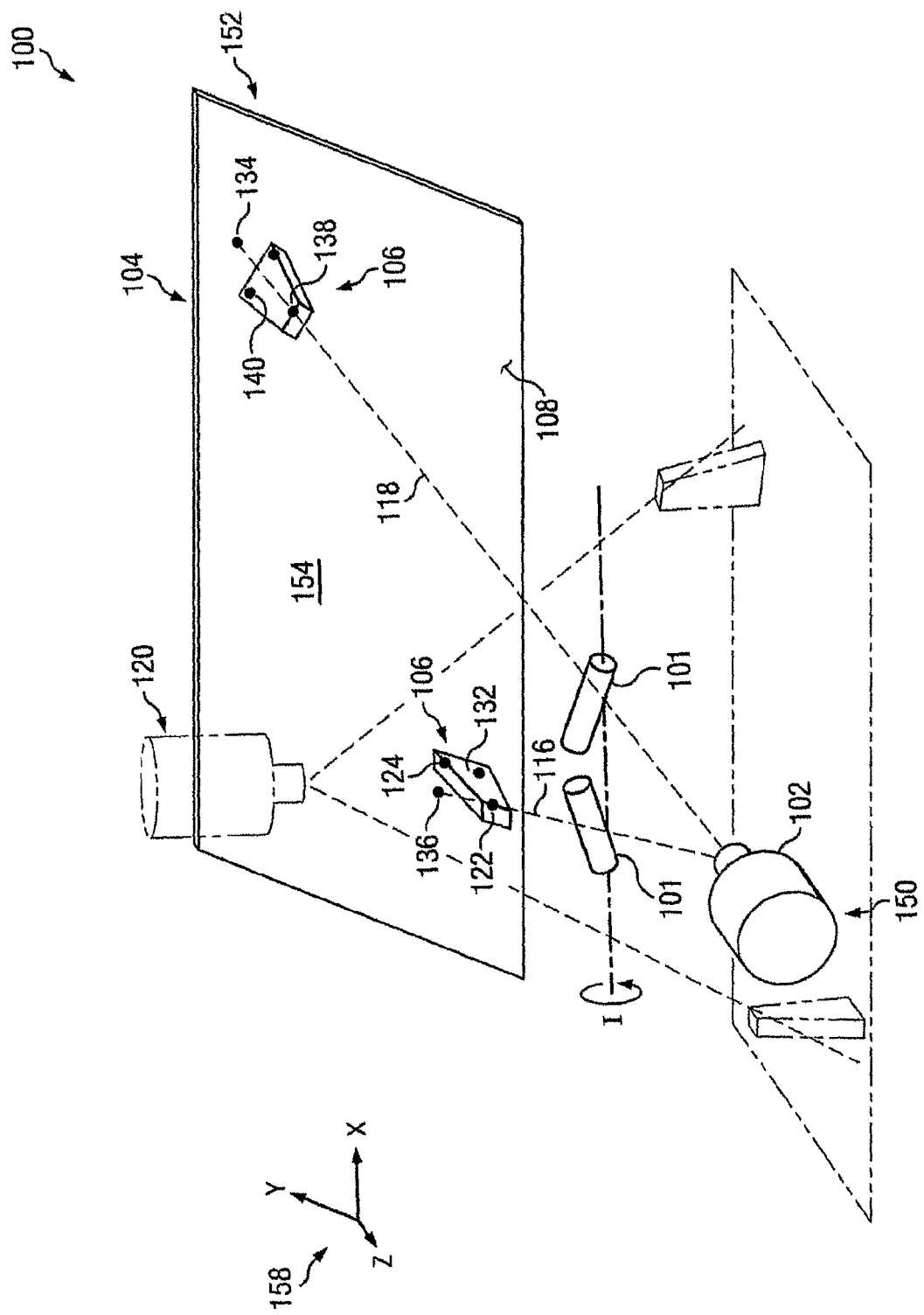
FIG. 2C is another perspective view of the imaging system and the object shown in FIG. 2A in a second relative orientation, in accordance with the present disclosure.

In another embodiment, instead of rotating the object 101, the x-ray source 102 and the imager 104 can be rotated about the object 101 to achieve the second relative orientation 150 as shown in FIG. 2C. According to an exemplary embodiment, the x-ray source 102 and the imager 104 are rotated orthogonally about the object 101 and an imaging axis I passing through the object 101, in which case, the first and second relative orientations 120 and 150 are orthogonal. In this embodiment, a sensor such as an accelerometer can be attached to the x-ray source 102 and/or the imager 104. The sensor can be used to determine when the combined x-ray source 102 and imager 104 have been moved to an orientation that is orthogonal to the original orientation. According to this embodiment, the sensor emits a signal when the x-ray source 102 and/or the imager 104 arrive at an orientation that is orthogonal to the original orientation. The sensor may be further operable to provide a signal when the x-ray source 102 and/or the imager 104 are unintentionally rotated about axes other than the imaging axis I, thereby alarming a technician to correct the unintentional rotational movement.

According to another exemplary embodiment, the x-ray source 102 and the imager 104 are rotated about the object 101 and an imaging axis I passing through the object 101 such that the first and second relative orientations 120 and 150 are oblique with respect to each other. In this embodiment, a sensor such as an accelerometer may be attached to the x-ray source 102 and/or the imager 104. The sensor may be used to determine the angular rotation of x-ray source 102 and imager 104 relative to the object 101. The sensor may be further operable to provide a signal when the x-ray source 102 and/or the imager 104 are unintentionally rotated about axes other than the imaging axis I, thereby alarming a technician to correct the unintentional rotational movement. It is to be appreciated that the sensor may include an accelerometer, a calibrated level, or any other suitable device either described in the present disclosure or known in the art for measuring angular rotations.

Referring back to FIG. 2A, the x-ray source 102 in the first relative orientation 120 is operable to provide x-rays along a first path (not shown). One skilled in the art will appreciate that the term "first path" refers to the range of various trajectories of the x-rays emanating from the x-ray source 102 in the first orientation 120. For example, in the embodiment illustrated in FIG. 2A, the first path includes x-ray trajectories represented by lines 116 and 118 and the many lines residing therebetween. In the first orientation, the imager 104 is disposed in the first path and oriented such that the imaging surface 108 and the reference marker 106 are both facing toward the x-ray source 102. Such an orientation of the imaging surface 108 and the reference marker 106 corresponds to a first imaging orientation 120. The first roentgenogram of the reference marker 106 in the first imaging orientation 120 can be obtained by directing x-rays along the first path through the object 101 toward the imager 104 in the first path. As such, the first roentgenogram includes projections of the reference markers 106 and 107 and the object 101 in a first plane 126 defined by the imaging surface 108.

Referring to FIGS. 2B and 2C, the x-ray source 102 in the second relative orientation 150 is operable to provide x-rays along a second path (not shown). One skilled in the art will appreciate that the term "second path" refers to the range of various trajectories of the x-rays emanating from the x-ray source 102 in the second relative orientation 150. For example, in the embodiments illustrated in FIGS. 2B and 2C, the first path includes x-ray trajectories represented by lines 116 and 118 and the many lines residing therebetween. In the second relative orientation 150, the imager 104 is disposed in the second path and oriented such that the imaging surface 108 and the reference marker 106 are both facing toward the x-ray source 102. Such an orientation of the imaging surface 108 and the reference marker 106 corresponds to a second imaging orientation 150. The second roentgenogram of the reference marker 106 in the second imaging orientation 150 can be obtained by directing x-rays along the second path through the object 101 toward the imager 104 in the second path. As such, the second roentgenogram includes projections of the reference markers 106 and 107 and the object 101 in the first plane 126 defined by the imaging surface 108.

Figure 2D:
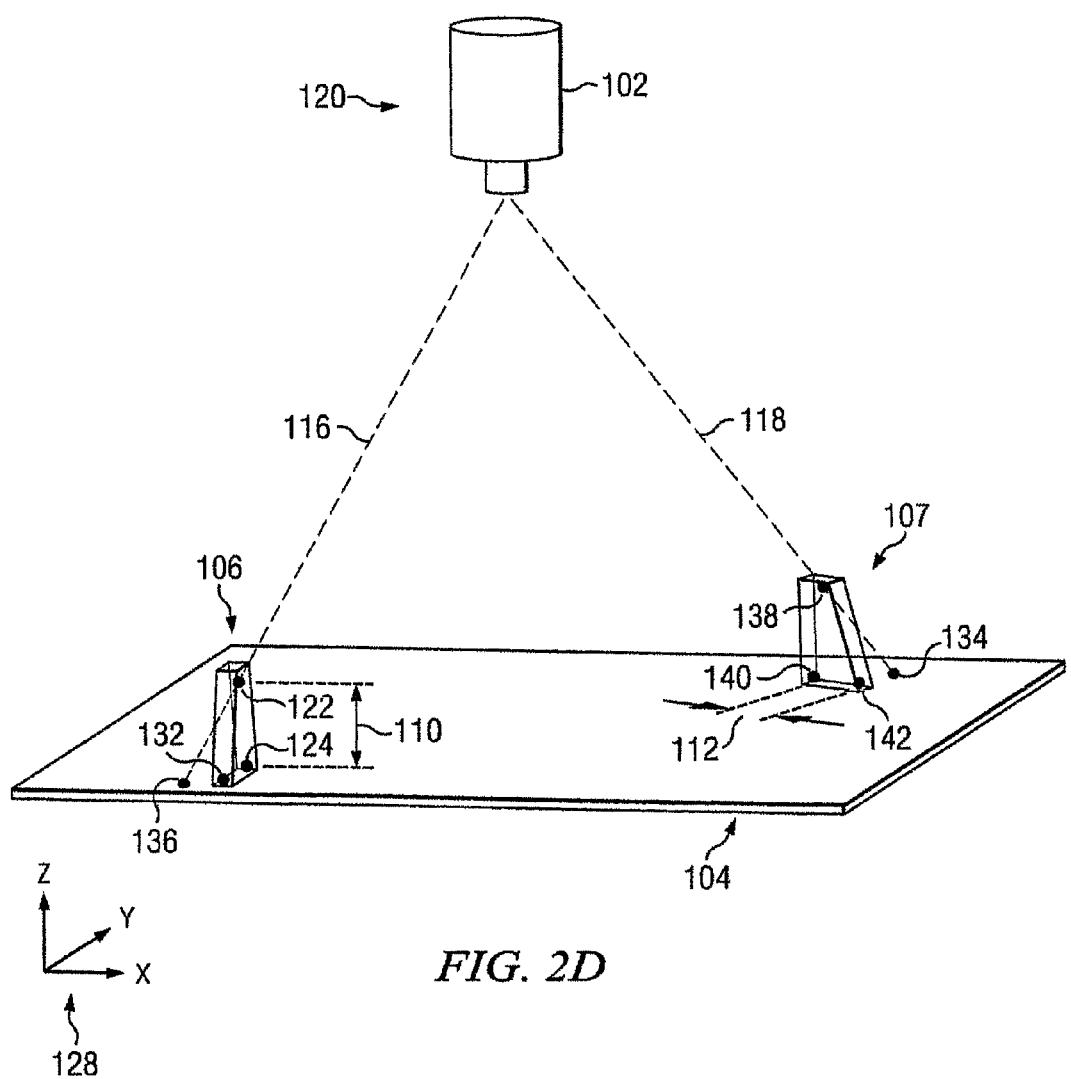
FIG. 2D is a schematic view of a light source in a first coordinate system, in accordance with the present disclosure.

The location of the x-ray source 102 with respect to the imager 104 can be determined by analyzing the shadows cast by the reference markers on the first and second roentgenograms. This analysis is described with reference to FIG. 2D, which is a simplified schematic illustration of the embodiment shown in FIG. 2A. In the illustrated embodiment, each of the depicted reference markers (106, 107) corresponds to the marker shown in FIG. 1C and comprises three fiducials 14 that define three points in a coordinate system 128: a top point (122, 138) a bottom point (124, 140) and a scale point (132, 142). The top points (122, 138) and the bottom points (124, 140) are aligned along a longitudinal axis (not shown) that is orthogonal to the surface of the imager 104. The distance between the top points (122, 138) and the bottom points (124, 140) in each of the respective markers (106, 107) is of a known distance 110 (e.g., 3, 5, 10, or 20 cm). The bottom points (124, 140) and the scale points (132, 142) of the markers (106, 107) are aligned along an axis parallel to the surface of the imager 104. The distance between the bottom points (124, 140) and the scale points (132, 142) in each of the respective markers (106, 107) is a known distance 112 (e.g., 1, 2, 5, or 10 cm). Although the second marker 107 is depicted as corresponding to the marker depicted in FIG. 1C, the marker depicted in FIG. 1B, which comprises two fiducials, may also be utilized. In some embodiments, a second marker 107 may not be used if the first marker 106 is a maker similar to the marker depicted in FIG. 1A, which includes three fiducials aligned in a longitudinal axis.

By examining the relationship between the positions of the fiducials in each of markers 106 and 107 and the shadows they cast on the first and second roentgenograms, the 3-D location of the x-ray source 102 in the coordinate system 128 can be determined. With reference to marker 106 in FIG. 2A, the position of top point 122 above the imager 104 in the coordinate system 128 can be calculated by identifying a point that is distance 110 above the bottom point 124. Next, a vector 116 can be constructed based on two points in space: top point 122 and shadow 136, which is the projection of top point 122 on the imager 104. This vector 116 can be mathematically determined using known triangulation and trigonometric techniques, and it identifies a trajectory from the x-ray source 102 that created the shadow 136 on the imager 104. As such, the x-ray source 102 is positioned somewhere along the vector 116, but the specific location of the x-ray source 102 along the vector 116 remains unknown. To determine the location of the x-ray source 102, a second vector 118 is constructed based on location of the top point 138 (as determined from the location of bottom point 140 and distance 110) and the shadow 134 casted by the top point 138. This second vector 118 also can be mathematically determined using known triangulation and trigonometric techniques. The intersection of the two vectors 116 and 118, in turn, identifies, or reasonably approximates, the 3-D location of the x-ray source 102 in the coordinate system 128.

It is to be appreciated that in some cases, the resolution of the first and second roentgenograms may not be enough to allow one to precisely identify the positions of the shadows 134 and 136 created by the top points 138 and 122, respectively. As a result, small errors may exist and cause the vectors/trajectories 116 and 118 to misalign and not intersect. In such cases, the position of the x-ray source 102 may be determined using an approximation model. According to an exemplary approximation model, the orientation and position of a segment between the vectors/trajectories 116 and 118 may be determined, and a point on the segment may be chosen to represent the position of the x-ray source 102. In an embodiment, the segment chosen may be a common perpendicular of the vectors/trajectories 116 and 118, and the midpoint of the common perpendicular may be chosen to represent the position of the x-ray source 102. It is to be appreciated that while a common perpendicular of both vectors/trajectories 116 and 118 may be the shortest segment between the vectors/trajectories 116 and 118 and may allow for an accurate approximation of the x-ray source 102, other segments may also be chosen, depending on the desired accuracy of the approximation model.

In an exemplary embodiment, the common perpendicular of the vectors/trajectories 116 and 118 may be determined by using the mathematical model discussed below, in which it is assumed that $(x^1_1, y^1_1, z^1_1)$ are the coordinates of the top point 1 shadow (136), $(x^1_2, y^1_2, z^1_2)$ are the coordinates of the top point 1 (122), $(x^2_1, y^2_1, z^2_1)$ are the coordinates of the top point 2 shadow (134), $(x^2_2, y^2_2, z^2_2)$ are the coordinates of the top point 2 (138). The equation for the first line 116 may thus be expressed as:

$$\frac{x - x^1_2}{x^1_2 - x^1_1} = \frac{y - y^1_2}{y^1_2 - y^1_1} = \frac{z - z^1_2}{z^1_2 - z^1_1} \quad (1)$$

and the equation for the second line 118 may be expressed as:

$$\frac{x - x^2_2}{x^2_2 - x^2_1} = \frac{y - y^2_2}{y^2_2 - y^2_1} = \frac{z - z^2_2}{z^2_2 - z^2_1} \quad (2)$$

The resulting vectors of the first line 116 and second line 118 may respectively be represented as:

$$\vec{a} = (a_p, a_2, a_3)$$

$$\vec{b} = (b_p, b_2, b_3) \quad (3)$$

where:

$$a_1 = x_2^1 - x_1^1,$$

$$a_2 = y_2^1 - y_1^1$$

$$a_3 = z_2^1 - z_1^1$$

$$b_1 = x_2^2 - x_1^2$$

$$b_2 = y_2^2 - y_1^2$$

$$b_3 = z_2^2 - z_1^2$$

Multiplying vectors a and b according to the equation below would provide a vector c that is perpendicular both lines 116 and 118:

$$\vec{c} = [\vec{a} \times \vec{b}] \quad (4)$$

$$= \begin{vmatrix} \vec{i} & \vec{j} & \vec{k} \\ a_1 & a_2 & a_3 \\ b_1 & b_2 & b_3 \end{vmatrix}$$

$$= \vec{i} * (a_2 * b_3 - b_2 * a_3) + \vec{j} * (b_1 * a_3 - a_1 * b_3) + \vec{k} * (a_1 * b_2 - b_1 * a_2)$$

where i, j, and k are unit vectors directed along the coordinate axes x, y, and z.

$$\vec{c} = (c_1, c_2, c_3)$$

$$c_1 = (a_2 * b_3 - b_2 * a_3)$$

$$c_2 = (b_1 * a_3 - a_1 * b_3)$$

$$c_3 = (a_1 * b_2 - b_1 * a_2) \quad (5)$$

In an embodiment, approximating the location of the x-ray source 102 may involve defining a segment S that lies in vector c and connects lines 116 and 118. As such, the segment S is a common perpendicular to the lines 116 and 118. One way of doing so is to build a plane D that includes the top point 1 shadow (136), the first line 116, and the vector c. A perpendicular vector to such a plane D is the product of vector multiplication $[\vec{a} \times \vec{c}]$, and may be expressed as:

$$\vec{n}' = [\vec{a} \times \vec{c}] \quad (6)$$

$$= \begin{vmatrix} \vec{i} & \vec{j} & \vec{k} \\ a_1 & a_2 & a_3 \\ c_1 & c_2 & c_3 \end{vmatrix}$$

$$= \vec{i} * (a_2 * c_3 - c_2 * a_3) + \vec{j} * (c_1 * a_3 - a_1 * c_3) + \vec{k} * (a_1 * c_2 - c_1 * a_2)$$

$$n'_1 = (a_2 * c_3 - c_2 * a_3)$$

$$n'_2 = (c_1 * a_3 - a_1 * c_3)$$

$$n'_3 = (a_1 * c_2 - c_1 * a_2)$$

This vector can be normalized with respect to a unit length and expressed as:

$$\vec{n} = \frac{\vec{n}'}{\|\vec{n}'\|} \quad (7)$$

$$\|\vec{n}'\| = \sqrt{(n'_1)^2 + (n'_2)^2 + (n'_3)^2}$$

$$n_1 = \frac{(a_2 * c_3 - c_2 * a_3)}{\|\vec{n}'\|}$$

$$n_2 = \frac{(c_1 * a_3 - a_1 * c_3)}{\|\vec{n}'\|}$$

$$n_3 = \frac{(a_1 * c_2 - c_1 * a_2)}{\|\vec{n}'\|}$$

A plane D going through the top point 1 shadow (136) having coordinates $(x_1^1, y_1^1, z_1^1)$ and having a perpendicular vector $\vec{n} = (n_1, n_2, n_3)$ may thus be represented by the following equations:

$$n_1 * x + n_2 * y + n_3 * z + D = 0$$

$$D = n_1 * x_1^1 + n_2 * y_1^1 + n_3 * z_1^1 \quad (8)$$

One of the endpoints of the segment S may be the crossing point where the plane D intersects with line 118. To determine the location of this crossing point, a right triangle may be drawn such that its hypotenuse G extends along line 118 and connects the top point 2 shadow 134 and the crossing point at which line 118 intersects the plane D. Furthermore, a first leg R of the right triangle may be defined by a vector r perpendicular to plane D and extending from the top point 2 shadow 134 to the plane D. The second leg of the right triangle may be defined by the projection of the hypotenuse G in the plane D.

The length of the first leg R, which is distance between top point 2 shadow 134 and the plane D, may be determined by a scalar multiplication of plane D's normalized perpendicular vector n and the vector r. In this case, the product of this scalar multiplication may be expressed in terms of the coordinates of the "top point 2 shadow 134" as illustrated in equation (9) below:

$$R = (\vec{n} \cdot \vec{r}) = n_1 \cdot x_1^2 + n_2 \cdot y_1^2 + n_3 \cdot z_1^2 \quad (9)$$

Furthermore, the cosine of the angle φ between the vector r and the vector b may be expressed as:

$$\cos\phi = \frac{(\vec{b} \cdot \vec{n})}{|\vec{b}| \cdot |\vec{n}|} \quad (10)$$

$$= \frac{b_1 * n_1 + b_2 * n_2 + b_3 * n_3}{\sqrt{(b_1)^2 + (b_2)^2 + (b_3)^2} * \sqrt{(n_1)^2 + (n_2)^2 + (n_3)^2}}$$

Accordingly, the length of the hypotenuse G can be determined by dividing the length of the first leg R by the cosine of the angle between the first leg R and hypotenuse G:

$$G = \frac{R}{|\cos\phi|} \quad (11)$$

In order to find coordinates of the crossing point where line 118 intersects the plane D, a vector $\vec{L}$ extending along line 118 may be defined from the top point 2 shadow 134 and a length of G:

$$\vec{L} = G * \frac{\vec{b}}{\|\vec{b}\|} \quad (12)$$

$$= \vec{i} * \frac{G * b_1}{\sqrt{(b_1)^2 + (b_2)^2 + (b_3)^2}} + \vec{j} * \frac{G * b_2}{\sqrt{(b_1)^2 + (b_2)^2 + (b_3)^2}} + \vec{k} * \frac{G * b_3}{\sqrt{(b_1)^2 + (b_2)^2 + (b_3)^2}}$$

$$\vec{L} = \vec{i} * L_1 + \vec{j} * L_2 + \vec{k} * L_3$$

where $$x' = x_1^2 + L_1$$

$$y' = y_1^2 + L_2$$

$$z' = z_1^2 + L_3 \quad (13)$$

These coordinates define one of the endpoints of segment S. In order to find coordinates of the second endpoint of segment S, similar calculations may be performed. In an embodiment, a plane may be defined along the line 118 and finding the crossing point of this plane the line 116. In an embodiment, after defining the endpoints of the segment S, the positioning of the x-ray source 102 may be approximated to be located in the middle of segment S and calculated as the mean of those coordinates:

$$x_{light} = \frac{x' + x''}{2} \quad (14)$$

$$y_{light} = \frac{y' + y''}{2}$$

$$z_{light} = \frac{z'' + z''}{2}$$

It is to be appreciated that in other embodiments, the approximated location of the x-ray source 102 may be anywhere between the endpoints of the segment S. It is to be further appreciated that while the above discussed exemplary mathematical model provides an efficient and precise method of approximating the location of x-ray source 102, other suitable models according to the principles of the present disclosure may also be used to approximate the location of x-ray source 102.

It is to be appreciated that the roentgenogram disclosed in the present disclosure may be a digital roentgenogram, and the coordinates may be initially scaled by pixels of the digital roentgenogram. The digital roentgenogram may be received originally in digital format, or it may be digitized from an x-ray image on a physical film. In the embodiments in which the roentgenogram was received originally in digital format, a scaling factor for converting the number of pixels to measurable distance may be predetermined. In the embodiments in which the roentgenogram was digitized from an x-ray image on a physical film, the coordinates of the coordinate system 128, however, can be converted to measurable length scale by identifying a scaling factor between the number of pixels and the length each pixel represents. In an exemplary embodiment, the scaling factor can be found by measuring the distance 112 between the bottom point 124 and a scale point 132 and the number of pixels between these two points.

Furthermore, in some embodiments, an appreciable distance can exist between the bottom fiducials (124, 132, 140, 142) and the actual surface of the imager 108. This may be case if the reference marker 106 is not directly mounted on the imager 104, or if the fiducials 14 are not disposed proximate to the bottom surface of the marker 106. This situation may also arise when an x-ray cassette is positioned a measurable distance below the top surface of the imager 104. In this situation, reference markers having more than one fiducial on the bottom surface can be utilized (e.g., the marker depicted in FIG. 1C). The roentgenogram of these reference markers can be used to determine the magnification (if any) of the corresponding roentgenogram. After determining the scaling factor as discussed above, known triangulation and trigonometric techniques may be used along with the predetermined or calculated scaling factor can be used to calculate the distance between the bottom surface of the markers and the actual plane of the imager 108 and the magnification ratio.

Figure 2E:
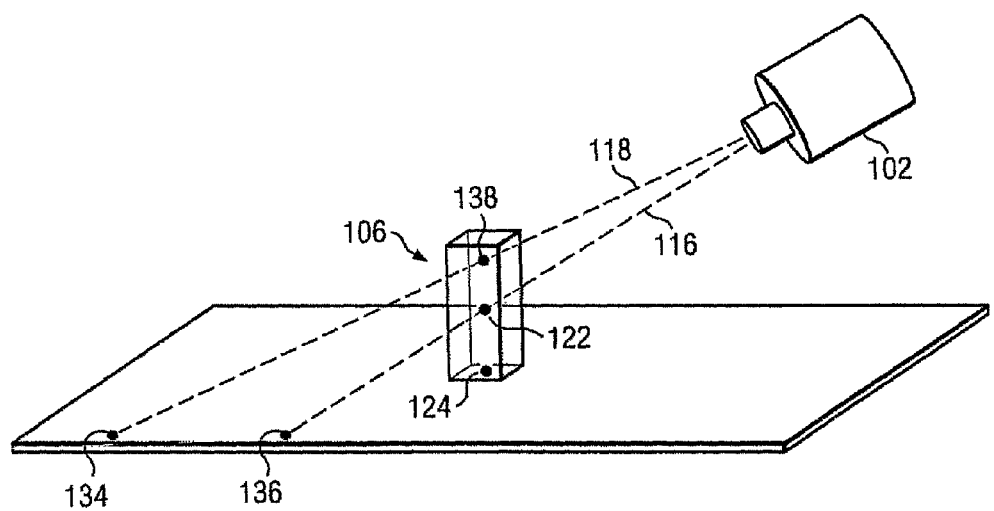
FIG. 2E is a perspective view of a light source and the reference marker shown in FIG. 1A in a first coordinate system, in accordance with the present disclosure.
Figure 2E:
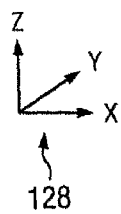

The technique described above can be implemented using different types and number of markers 106. For example, in an embodiment in which the calibration factor is determined without using a marker, the markers 106 may comprise a pair of the markers 10 depicted in FIG. 1B, in which the markers 10 each comprise only two fiducials 14. Furthermore, instead of using a pair of markers (106, 107), one marker 106 configured as illustrated in FIG. 1A may be used. The marker 10 in FIG. 1A includes a first fiducial 14 proximate to the surface of an imager 104 when the marker 10 is disposed on the imager 104. Such a first fiducial 14 would define a bottom point 124 or 140 as discussed above. Since each of the three fiducials 14 in such a marker is placed at known distances from each other, the other two fiducials 14 would define two top points (122, 138) relative to the bottom point 124 or 140, and these two top points (122, 138) can be used to determine the position of the x-ray source 102. Accordingly, by triangulating the shadows (134, 136) cast by those fiducials 14, two corresponding vectors 116 and 118 that are pointed in the direction of the x-ray source 102 can be determined as shown in FIG. 2E. By identifying the intersection of those two vectors, the 3-D position of the x-ray source 102 can be calculated as discussed above.

In an exemplary embodiment, the first and second roentgenograms are digital roentgenograms either directly generated using a computer (not shown) or converted from conventional roentgenograms using techniques known in the art, such as scanning the roentgenograms into the computer or using a digital pen to trace the projections in the roentgenograms. In some embodiments, the computer comprises a memory unit for receiving and storing the roentgenograms, and a controller operable to create a three-dimension model of the object depicted in the roentgenograms in a 3-D space as discussed below. Further examples of systems suitable for providing first and second digital roentgenograms are described below with respect to FIG. 12.

Figure 3A:
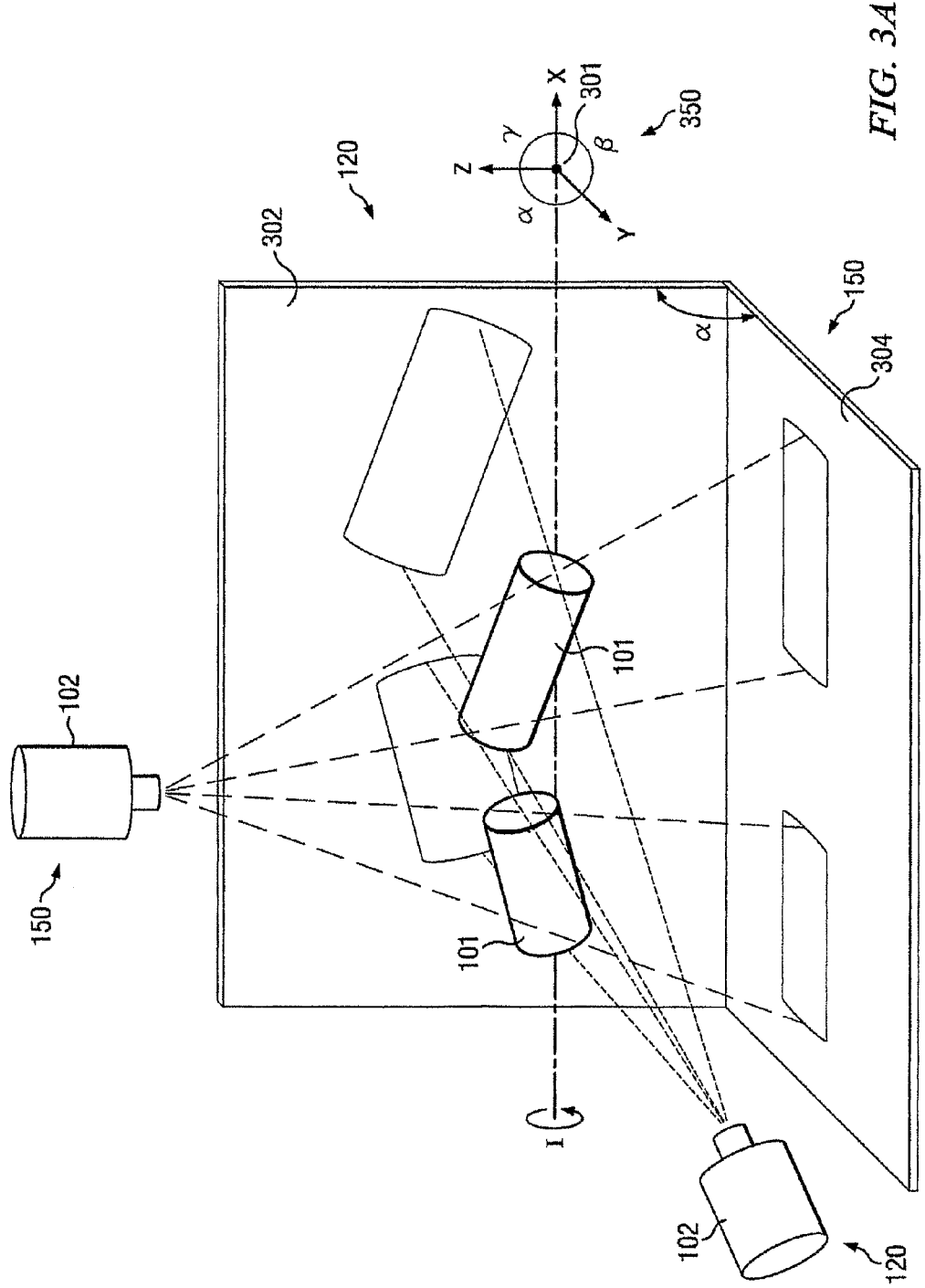
FIG. 3A is a schematic diagram illustrating first and second roentgenograms of an object, in accordance with the present disclosure.

Once the 3-D location of the x-ray source 102 in the first and second imaging orientations (120, 150) has been identified, a variety of different techniques can be used to create a 3-D model of the imaged object. According to one embodiment, the amount of angular displacement about the imaging axis I between the first imaging orientation 120 and the second imaging orientation 150 is known. Illustrations corresponding to this embodiment are depicted in FIGS. 3A-3G. FIG. 3A depicts objects 101 that are being imaged at two orientations (120, 150). The images at the two relative orientations (120, 150) can be prepared by either rotating the imaged object 101 about an imaging axis I by angular displacement α, or by rotating the x-ray source and the imager about the imaging axis I by an angular displacement α. Preferably but not required, the imaging axis I is parallel to the plane of the x-ray imager (not shown) in the first orientation 120 and to the plane of the x-ray imager in the second orientation 150. Creating these images at two orientations will result in two roentgenograms (302, 304) that correspond to orientations 120, 150, respectively. Also shown in FIG. 3A are the relative positions of the x-ray sources 102 with respect to the roentgenograms (302, 304). The 3-D positions of these x-ray sources 102 may be determined based upon the shadows created by the reference markers on the roentgenograms (302, 304), as described above, or by any other techniques known in the art, such as physically measuring the position of the x-ray source 102 with respect to the imager 104.

Another step in the creation of a 3-D model of the objects 101 is to determine the outline of the imaged objects 101 in the roentgenograms. This concept is depicted in FIG. 3B, in which the outlines of the imaged object in the first roentgenogram 302 have been identified as outlines 303. Similarly, the outlines of the imaged object in the second roentgenogram 304 have been identified as outlines 305. Where the roentgenograms are digital images stored in a computer system, this process can be performed automatically by using image-processing software. According to another embodiment, this process can be performed manually by tracing the outline of the imaged object in the roentgenograms with a mouse, a stylus, or any other tracing device. After determining the outline of the imaged object and the 3-D position of the x-ray source 102, a projection of the outline of the imaged object can be created. The projection of the object outline 303 in the first orientation 120 is depicted in FIG. 3B by projection lines 308, which pass from the outline 303 in the first roentgenogram 302 to the 3-D position of the x-ray source 102 in the first orientation 120. Similarly, the projection of the object outline 305 in the second orientation 150 is depicted in FIG. 3B by projection lines 306, which pass from the outline 305 in the second roentgenogram 304 to the 3-D position of the x-ray source 102 in the second orientation 150.

Once the projections of the imaged objects have been created for the first and second orientations (120, 150), the relative position of the orientations (120, 150) with respect to each other may be used to determine how those projections intersect with each other. This can be done in a variety of ways. According to one embodiment, the 3-D projections may be combined into a single 3-D reference frame corresponding to the x, y, z reference frame 350 depicted in FIGS. 3A-3E. The origin for the x, y, z reference frame 350 may be located along the imaging axis I at point 301 where the x-rays from the x-ray source 102 in the first orientation 120 intersect the imaging axis orthogonally and the x-rays from the x-ray source 102 in the second orientation 150 intersect the imaging axis orthogonally. As discussed above, in this reference frame 350, angle α corresponds to angular displacement between the two orientations (120, 150) about the x-axis, or the imaging axis I. This angle α can be determined in a variety of ways. In the embodiment where x-ray source 102 and the imager 104 are stationary and the object is rotated, the angle α corresponds to the amount of rotation of the object about the x-axis or imaging axis I, as shown in FIGS. 2A, 2B, and 3A. In an alternative embodiment where the object remains stationary, but the x-ray source 102 and the imager 104 are rotated about the object, the angle α corresponds to the amount of rotation of the x-ray source 102 and the imager 104 about the imaging axis I shown in FIGS. 2A, 2B, and 3A. When rotating the x-ray source 102 and the imager 104 about the imaged objects 101, it may be preferred, but not required, that the position of the x-ray source 102 be fixed with respect to the position of the imager 104. Further, it may be preferred, but not required, that the roentgenograms (302, 304) be taken at orientations (120, 150) that are substantially orthogonal with respect to each other. Using the angular displacement α and the projections of the outlines described above, the relative positions of the roentgenograms (302, 304) and their corresponding projections can be aligned with each other.

The angles β and γ correspond to the angular displacement of the first roentgenogram 302 with respect to the second roentgenograms 304 about the z- and y-axes, respectively. As discussed above, in some embodiments, the first and second relative orientations 120 and 150 are substantially orthogonal with respect to each other, and in these embodiments, the angles β and γ may be substantially zero. In embodiments in which first and second relative orientations 120 and 150 are not substantially orthogonal, first and second roentgenograms (302, 304) may be further aligned at angles β and γ using a variety of approaches, including the iterative approaches to be described in the present disclosure. It is to be appreciated that while it is optional to align the roentgenograms (302, 304) at angles β and γ, doing so may allow for a more accurate 3-D model of the object 101.

Figure 3C:
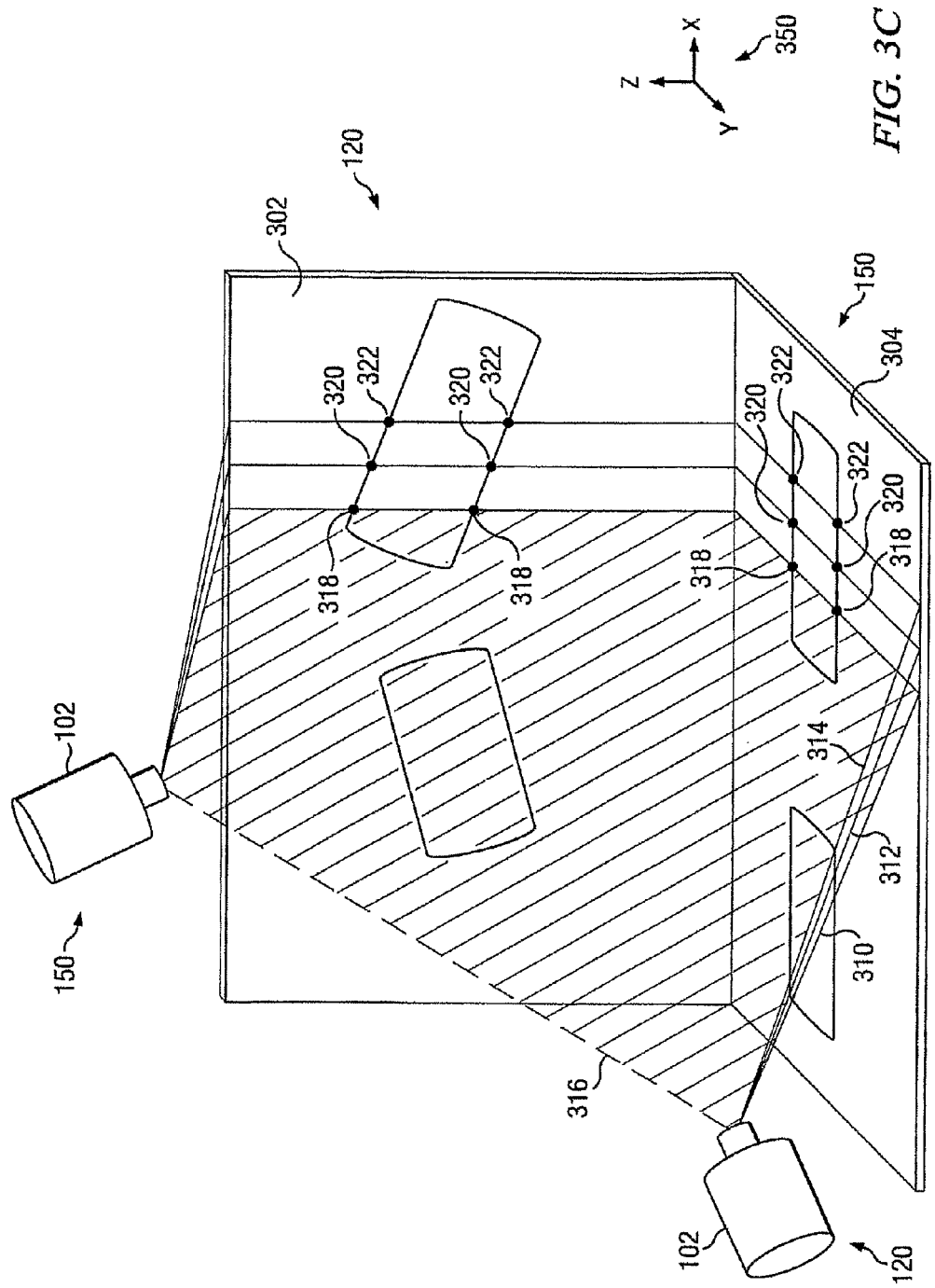
FIG. 3C is a schematic diagram illustrating a plurality of intersection planes each passing through a tilt axis and the first and second roentgenograms shown in FIG. 3A, in accordance with the present disclosure.

FIG. 3C illustrates that the roentgenograms (302, 304) of the imaged objects 101, as well as the 3-D object projections of the imaged objects 101, may be intersected by a plurality of planes, including planes 310, 312, and 314. Each of these planes pass through a first 3-D position in the 3-D reference frame that corresponds to the location of the x-ray source 102 in the first orientation 120, and a second 3-D position in the 3-1) reference frame that corresponds to the location of the x-ray source 102 in the second orientation 150. FIG. 3C also depicts a tilt axis 316 that passes between the first and second 3-D positions in the 3-D reference frame. Each of the planes 310, 312, and 314 has a different tilt about the tilt axis 316, such that they intersect the outlines of the imaged object 101 in the first and second roentgenograms (302, 304). The location of the intersections between plane 310 and the image outlines in the first and second roentgenograms (302, 304) is marked with points 318. The location of the intersections between plane 312 and the image outlines in the first and second roentgenograms (302, 304) is marked with points 320. The location of the intersections between plane 314 and the image outlines in the first and second roentgenograms (302, 304) is marked with points 322.

Figure 3D:
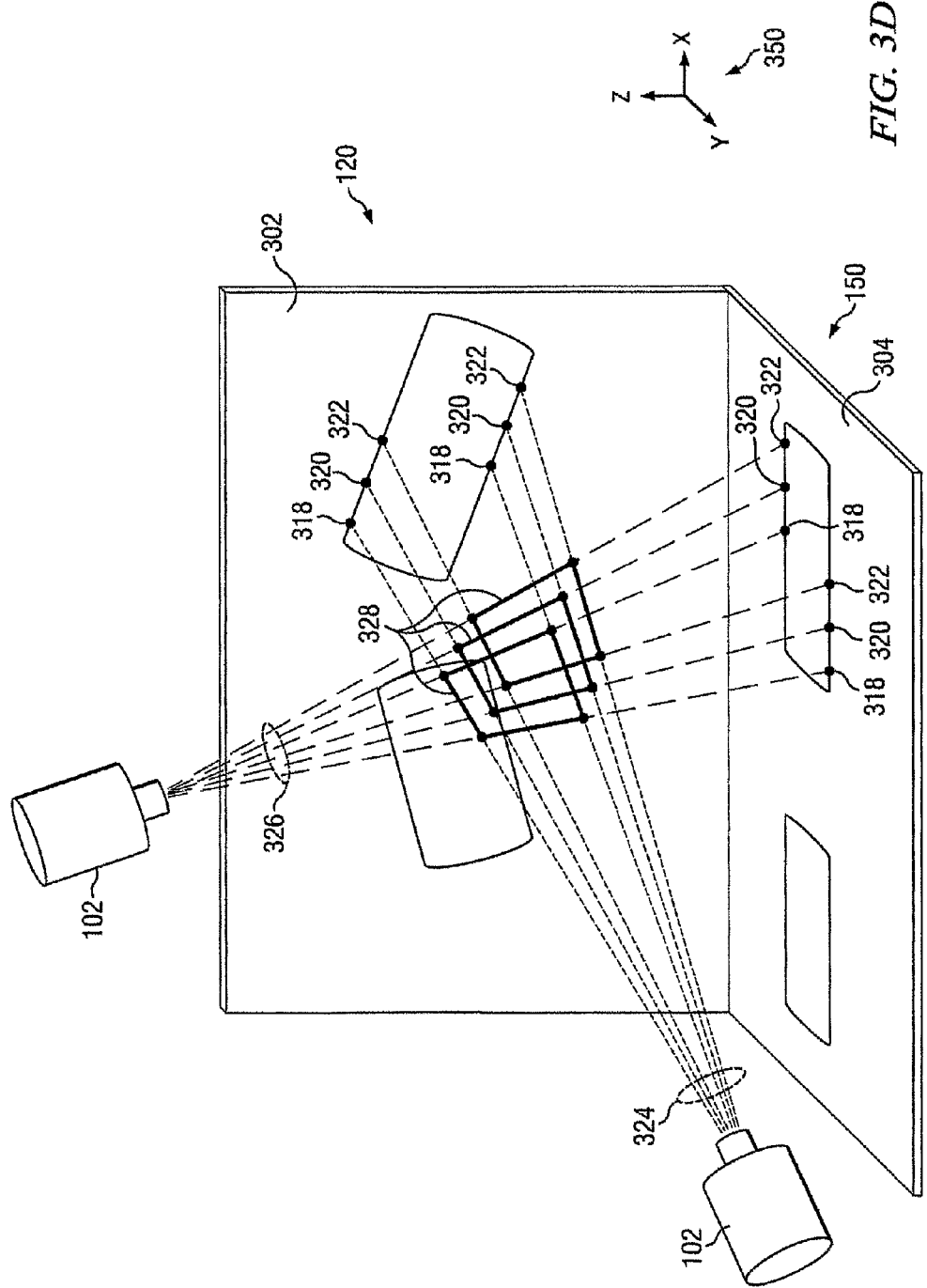
FIG. 3D is a schematic diagram illustrating a plurality of intersection points between the 3-D object projections from the first and second roentgenograms shown in FIG. 3A, in accordance with the present disclosure.

In FIG. 3D, each of the intersection points 318, 320, and 322 is connected to the location of the x-ray source 102 in the 3-D reference frame 350 at the corresponding orientations (120, 150). Accordingly, intersection points 318, 320, and 322 in roentgenogram 302 are connected by lines 324 to the first 3-D location in the 3-D reference frame 350, which corresponds to the location of the x-ray source 102 in the first orientation 120. Similarly, intersection points 318, 320, and 322 in roentgenogram 304 are connected by lines 326 to the second 3-D location in the 3-D reference frame 350, which corresponds to the location of the x-ray source 102 in the second orientation 150. The four lines intersecting the set of points 318 in the first and second roentgenograms (302, 304) also intersect with each other to form a polygon 328 in 3-D reference frame 350. Similarly, the four lines intersecting the set of points 320 in the first and second roentgenograms (302, 304) also intersect with each other to form a polygon 328 in 3-D reference frame 350. Further, the four lines intersecting the set of points 322 in the first and second roentgenograms (302, 304) also intersect with each other to form a polygon 328 in 3-D reference frame 350.

Figure 3E:
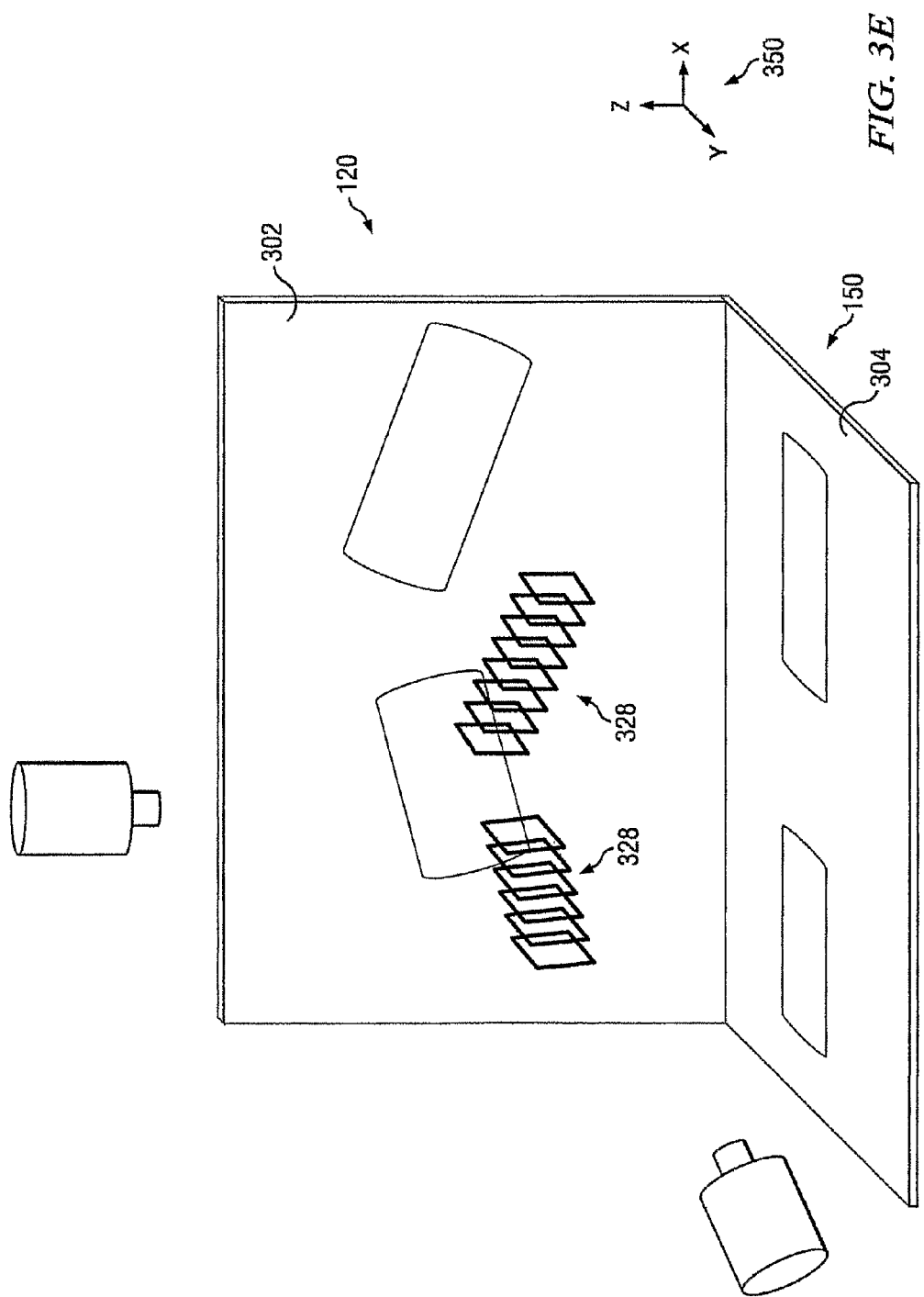
FIG. 3E is a schematic diagram illustrating a plurality of polygons connecting the intersection points in the intersection plane shown in FIG. 3D, in accordance with the present disclosure.

In FIG. 3E, the process of defining the polygons 328 may repeated for one or more planes aligned with the tilt axis 316 until a sufficient resolution is reached, or no further intersections with the imaged objects 101 are identified. Each of these polygons 328 corresponds to the intersection between the 3-D object projections in the first and second orientations (302, 304) in the 3-D reference frame 350.

Figure 3F:
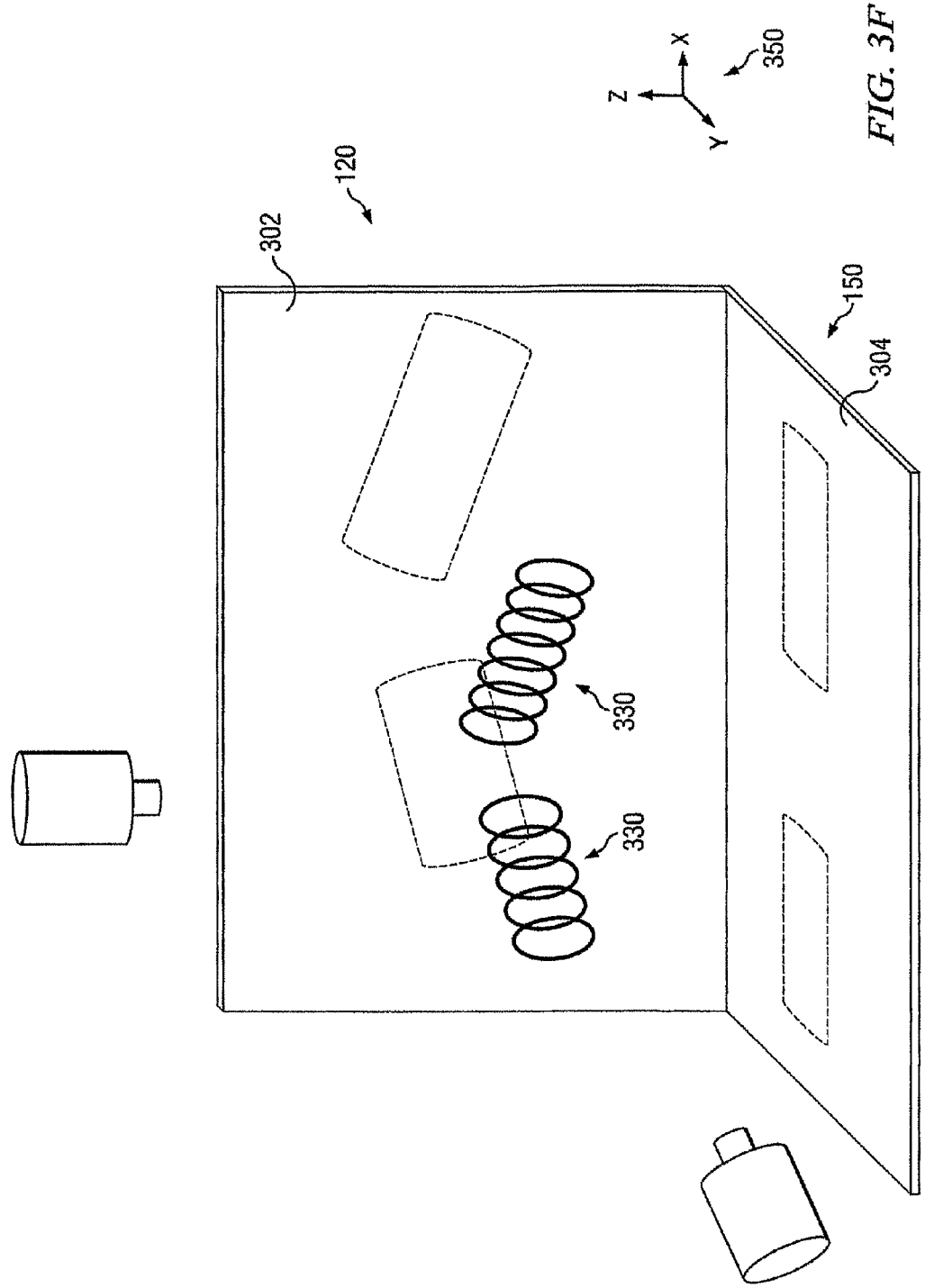
FIG. 3F is a schematic diagram illustrating a plurality of one or more closed curves within the each of the one or more polygons shown in FIG. 3E, in accordance with the present disclosure.
Figure 3G:
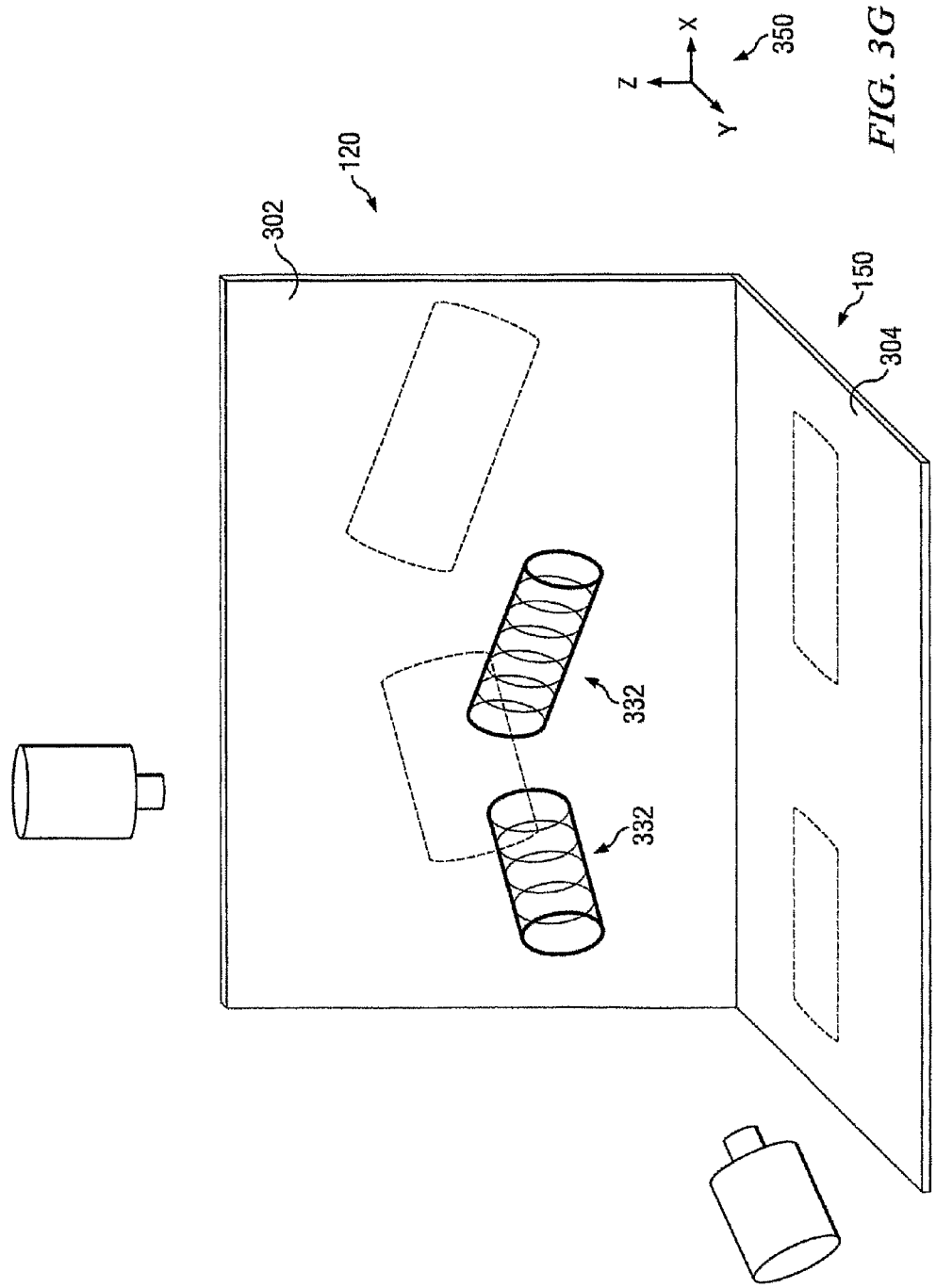
FIG. 3G is a schematic diagram illustrating a surface that connects each of the closed curves shown in FIG. 3F, in accordance with the present disclosure.

After creating a series of polygons 328 corresponding to the intersections of the 3-D projections, the polygons 328 may be converted into closed curves (e.g., ellipses) 330 that correspond to the cross section shape of the imaged objects 101 depicted in FIG. 3F. It is preferred, but not required, that the general shape and orientation of the imaged objects 101 be known before converting the series of polygons 328 into closed curves 330. For example, if the imaged object, such a bone, has a generally elliptical cross-sectional shape, then the polygons 328 can be replaced with closed curves 330, such as ellipses, that are located within each of the polygons. On the other hand, if the imaged object has a non-symmetrical shape, then other information about the imaged object (e.g., its shape, cross section, orientation, etc.) can be used to create an accurate 3-D model of the object. Once the polygons 328 have been replaced with corresponding shapes (e.g., closed curves or ellipses) 330, a surface connecting these shapes can be prepared. This surface may represent an accurate 3-D model 332 of the imaged object, as shown in FIG. 3G. In some embodiments, the accuracy of the 3-D model 332 may be enhanced by modifying the model 332 according to known shapes stored in an image library.

As discussed above, if the first and second relative orientations 120 and 150 are not substantially orthogonal, angles β and γ may be determined using iterative approach in accordance to the principles of the present disclosure. In an exemplary embodiment, roentgenograms (302, 304) may be orientated at angles β and γ by first aligning roentgenograms (302, 304) at a known α, and then creating various test 3-D models of the imaged objects 101 by aligning roentgenograms (302, 304) at various angle β and γ, and finally identifying a 3-D model that would produce 2-D projections that substantially match the outlines of the imaged object 101 in the first and second roentgenogram 302 and 304. The test models of the objects 101 may be created according to the approach described above with respect to FIGS. 3C-3G to provide better accuracy. It is to be appreciated, however, that the various test models may be generated according to any suitable modeling technique known in the art.

According to another embodiment, a 3-D model of an object can be created in a fixed reference frame even when the angular displacement α between two imaging orientations (120, 150) is not known. Illustrations corresponding to this embodiment are depicted in FIGS. 4A-4G. Much like the previously described process in which the angular displacement α is known, two roentgenograms are prepared of the object at different orientations. Each of these roentgenograms includes an image of the object 101 and an image of at least one reference marker (e.g., 106, 107) having at least two fiducials (e.g., 122, 124, 132, 138, 140, 142). In addition, the roentgenograms also include an image of at least one object marker 402 attached to the object 101. The at least one object marker 402 may be attached to the object 101 directly or indirectly, and the number of object marker 402 may vary depending on the number fiducials each contains. In an exemplary embodiment, a total of at least three fiducials are included in the at least one object marker 402. The at least three fiducials may be enclosed in one object marker 402, or distributed among a plurality of object markers 402, such as two or three object markers 402. In another exemplary embodiment, a total of four or more fiducials are included in the least one object marker 402, and the four or more fiducials may be enclosed in one marker 402 or distributed among a plurality of object markers 402, such as, two, three, four, or more, depending on the specific number of fiducials.

Figure 4A:
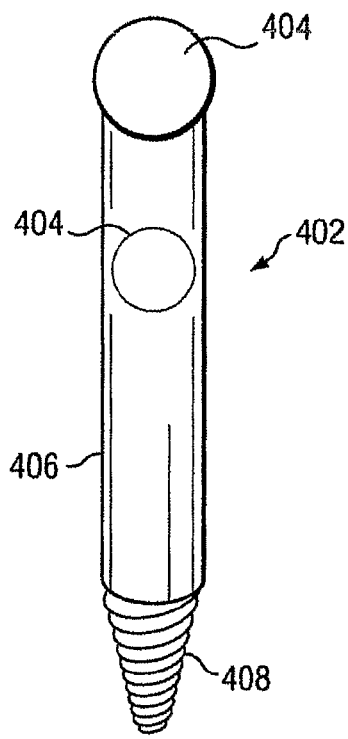
FIG. 4A is a perspective view of an embodiment of an object marker, in accordance with the present disclosure.

A variety of different object markers 402 may be used consistent with the disclosed embodiments. One representative example of an object marker 402 is depicted in FIG. 4A. In FIG. 4A, the object marker 402 comprises a fiducial 404, which may be in the shape of a sphere, and the fiducial 404 may be mounted on a post 406 that can be attached to the object 101 in a variety ways. In an example, the post 406 may be configured to include a threaded tip 408 that allows for easy coupling with a bone (not shown). As illustrated in FIG. 4A, in some embodiments, the post 406 may include additional fiducials 404, which may have the same size or different sizes. Fiducials 404 of a spherical shape may be preferred, but not required. It is to be appreciated the fiducial 404 may be made of a radio-opaque material that would allow it to be readily identifiable in an x-ray image. In an alternative embodiment, the marker 402 may be made of a radio-opaque material, and fiducial 404 may be a translucent portion in the marker 402. For example, the marker 402 may include a hole defined therethrough corresponding to a fiducial 404. Due to the contrast in radio-opacity, the defined hole may be readily identifiable in an x-ray image of the marker 402. It is to be appreciated that this configuration may be incorporated in any of the embodiments discussed in the present disclosure.

Figure 4B:
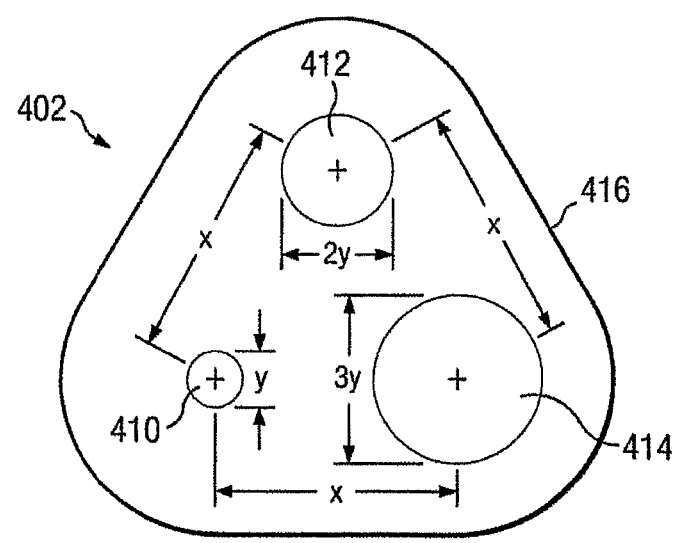
FIG. 4B is a perspective view of another embodiment of an object marker, in accordance with the present disclosure.

An alternative embodiment of an object marker 402 is depicted in FIG. 4B. In FIG. 4B, the object marker 402 comprises three fiducials 410, 412, and 414, which may preferably be in the shape of a sphere. The three fiducials 410, 412, and 414 may preferably mounted on a radio-translucent plate 416 at a fixed distance x (e.g., 6.0 cm) from each other. According to yet another embodiment, the sizes of the three fiducials 410, 412, and 414 have a fixed ratio with respect to each other. For example, in FIG. 4B, fiducial 410 has a diameter of size y (e.g., 0.5 cm), while fiducial 412 has a diameter of size 2y (e.g., 1.0 cm), and fiducial 414 has a diameter of size 3y (e.g., 1.5 cm). Alternatively, each of the fiducials may have varying shapes or degrees of radio-opaqueness, such that each of the fiducials can be individually identified. According to another embodiment, the object marker may be included into any of a variety of suitable orthopedic devices. Examples of suitable orthopedic devices include circular or monolateral external fixators, intramedullary nails, screws and plates. Each of these orthopedic devices may include radio-opaque portions that have fixed dimensions and spaced apart at known distances, which can be effective as object markers. In some embodiment, the orthopedic device itself may be used as an object marker 402.

Figure 4C:
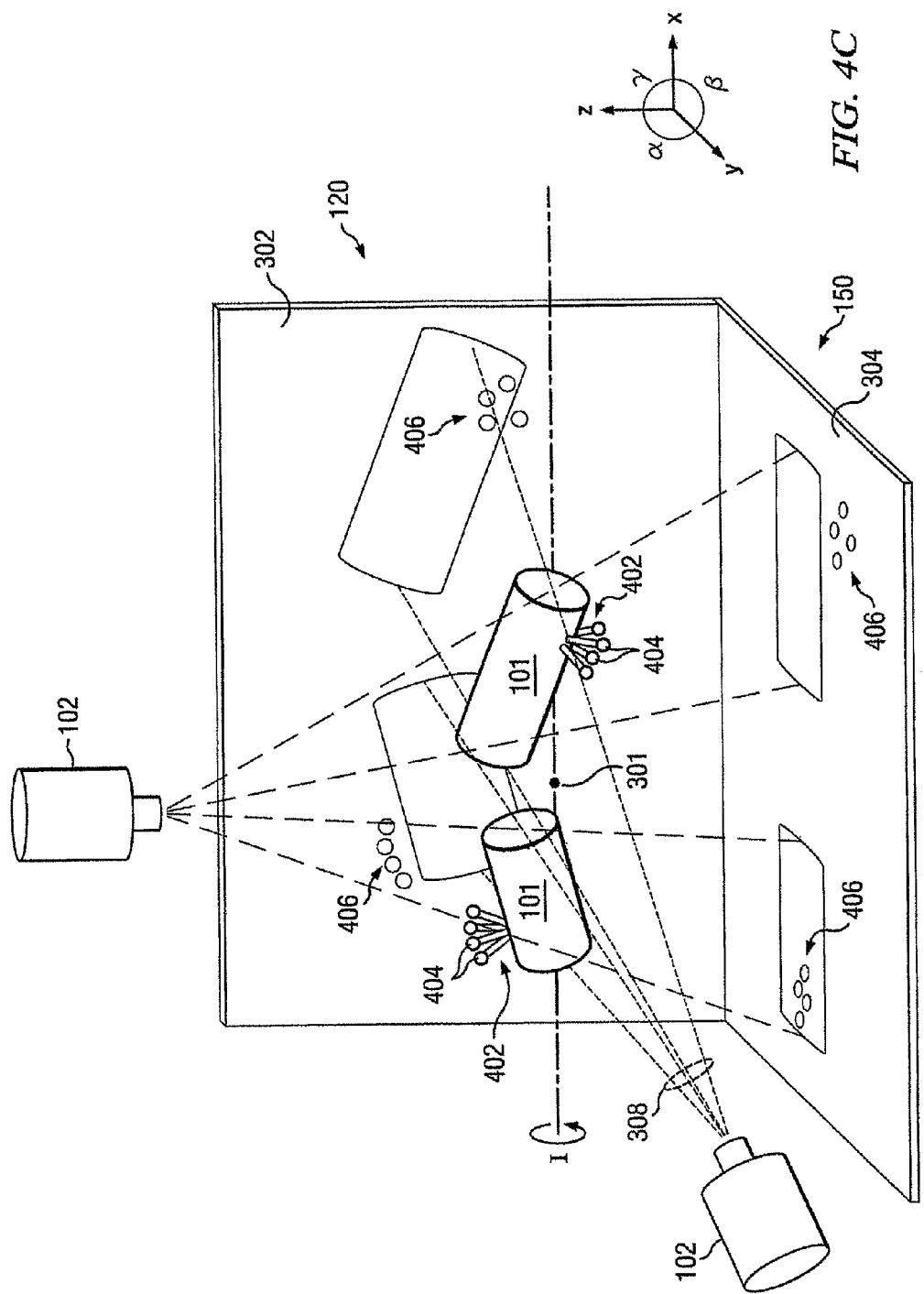
FIG. 4C is a schematic diagram illustrating a plurality of object markers being attached to an object, in accordance with the present disclosure.

An illustration of objects 101 with representative object markers 402 attached thereto is depicted in FIG. 4C. In FIG. 4C, imaged objects 101 each include four object markers 402 attached thereto, and each of these object markers 402 includes a fiducial 404. According to a first approach of using the object marker 402 to create a model of objects 101 in a fixed reference frame, the number and type of the object marker 402 may vary as long as there are at least three fiducials 404 directly or indirectly attached to at least one of the imaged objects 101. For example, in an embodiment, one object marker 402 may comprise three fiducials 404. In another exemplary embodiment, two object markers 402 may be used, each comprising two fiducials 404. In yet another exemplary embodiment, three object markers 402 may be used, each comprising one fiducial 404. While three fiducials 404 may be used in some embodiments, it is to be appreciated that embodiments using four or more fiducials 404 may be more desirable for reasons to be discussed below. It is to be further appreciated that according to the first approach of using the object marker 402 to create a model of objects 101 in a fixed reference frame, the positions of the fiducials 404 relative to each other are predetermined. In an exemplary embodiment, measurements may be taken to determine the length and orientation of the segments between fiducials 404. In another embodiment, the object markers 402 may be placed at predetermined orientations such that the positions of the fiducials 404 relative to each other can be predetermined. As such, the segments between the fiducials 404 can be mathematically determined.

In the embodiment depicted in FIG. 4C, the images of the object markers 402 are depicted in the corresponding roentgenograms 302 and 304. Upon receiving the two roentgenograms, the 3-D position of the x-ray source 102 with respect to the x-ray imager 104 may be determined for each imaging orientation (120, 150) in accordance with the principles disclosed in the present disclosure. In particular, these determinations may be based on the use of reference markers and fiducials in the same way as is described with respect to the previous embodiments. Similarly, outlines of the imaged objects 101 and shadow points 406 of fiducials 404 in the first and second roentgenograms (302, 304) may be identified using the same techniques described in the previous embodiment. At this point, different steps may be utilized to prepare a 3-D model of the imaged objects 101 using the object markers 402 and the fiducials 404.

Figure 4D:
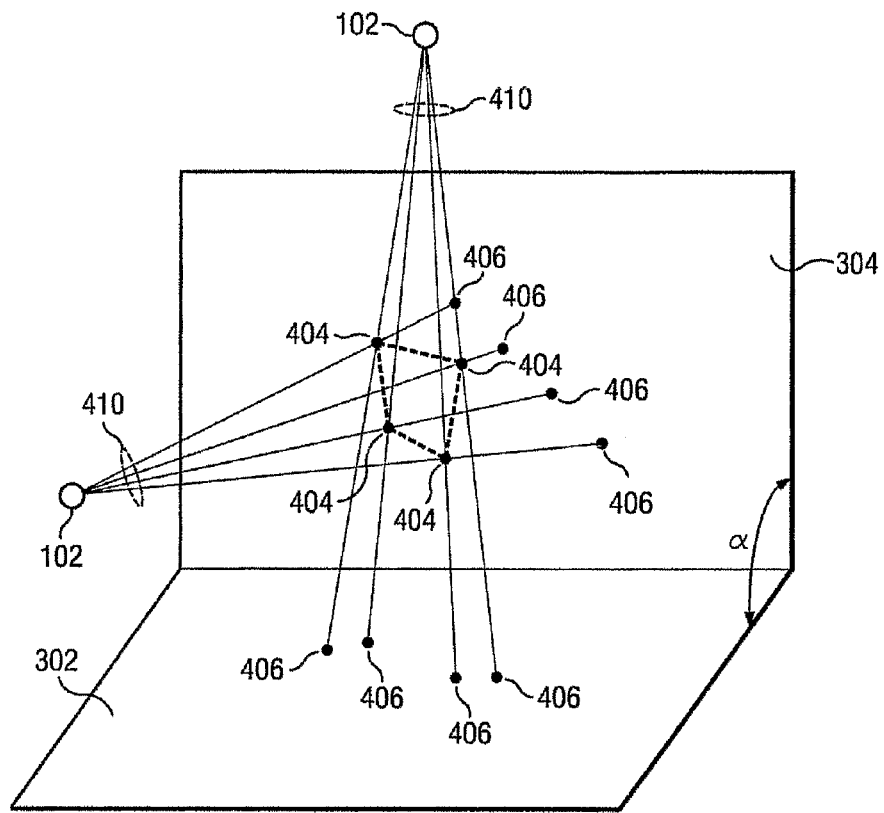
FIG. 4D is a schematic diagram illustrating projections of a plurality of fiducials from first and second roentgenograms to different light source locations, in accordance with the present disclosure.

Generally, the first approach of using the object marker 402 to create a model of objects 101 in a fixed reference frame includes constructing projection lines 410 connecting the shadow points 406 in roentgenograms (302, 304) and the location of the x-ray source 102 in their respective imaging orientations (120, 150), as depicted in FIG. 4D. The 3-D positions of the fiducials 404 relative to each roentgenogram (302, 304) may be mathematically determined based on the orientations of the projection lines 410 and the predetermined segments between the fiducials 404. In turn, the angular displacement α between the two imaging orientations 120 and 150 may be determined by aligning the 3-D positions of the fiducials 404 in a fixed reference frame. Once the displacement angle α has been identified, the process of creating a 3-D model of the imaged object may proceed in the same manner as was described with respect to FIGS. 3C-3G.

Figure 4E:
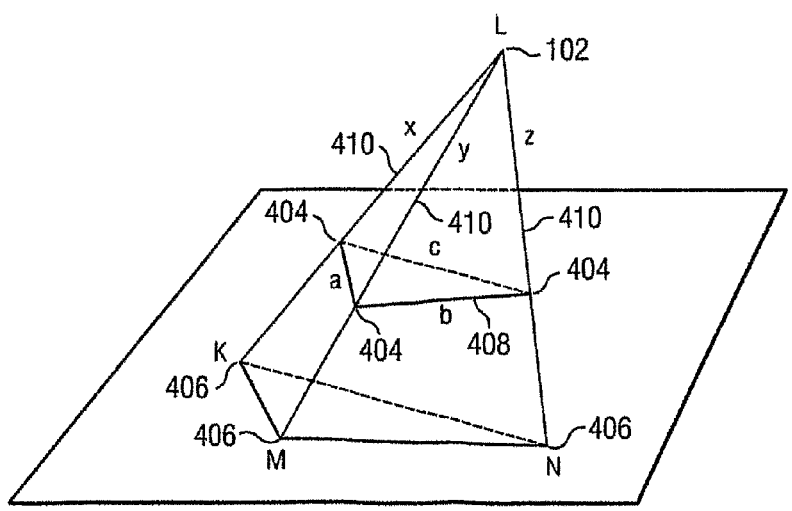
FIG. 4E is a schematic diagram illustrating a model of the fiducials shown in FIG. 4D in 3-D space, in accordance with the present disclosure.

It is to be appreciated that the determination of the 3-D positions of the fiducials 404 relative to each roentgenogram (302, 304) may be accomplished according to a variety of mathematical approaches. An exemplary mathematical approach is explored with reference to FIG. 4E. As discussed above, marker(s) (not shown) may be fixed to an object (not shown) in such a manner that positions of three fiducials 404 relative to each other may be predetermined. In the embodiment illustrated in FIG. 4E, shadow points 406 of the fiducials 404 in the roentgenogram 304 may be used to construct projection lines 410, which geometrically, may cooperate to form a three-sided pyramid. Additionally, since the positions of the corresponding fiducials 404 relative to each other have been predetermined, the dimensions of a triangle 408 formed by connecting the 3-D positions of the fiducials 404 may also be mathematically determined. As such, the following geometric elements may be established as shown in FIG. 4E: coordinates (L) of light source 102, coordinates (K, M, N) of shadow points 406, and the lengths of the legs (a, b, c) of triangle 408. To determine the 3-D position and orientation of the triangle 408, the exemplary approach of FIG. 4E may include rotating and "moving" the triangle 408 within the pyramid until it reaches a position where dimensions of the triangle 408 and the outer contour of the pyramid match. Based on known triangulation and trigonometric techniques, the position of the triangle 408 may correspond to the solution to the following equation system:

$$\begin{cases} a^2 = x^2 + y^2 - 2xy\cos\alpha \\ b^2 = y^2 + z^2 - 2yz\cos\beta \\ c^2 = z^2 + x^2 - 2zx\cos\gamma \end{cases}$$

in which, angles KLM, MLN, KLN correspond α, β, and γ, respectively, and x, y, z correspond to the distance between the light source and the fiducials 404. Mathematically, this system of equations has 8 different solutions, but some of them may include complex and negative numbers, and thus may be eliminated. As such, there may be two solutions remaining that may correctly reflect the position of the fiducials 404. It is, however, difficult to mathematically determine which one out of remaining two solutions is correct. In an embodiment, 3-D models of the image object based on both solutions may be presented to a person, who may then visually determine and select the model that matches the orientation of the imaged object. In orthopedic application, the person selecting the matching model may be a physician.

Figure 4F:
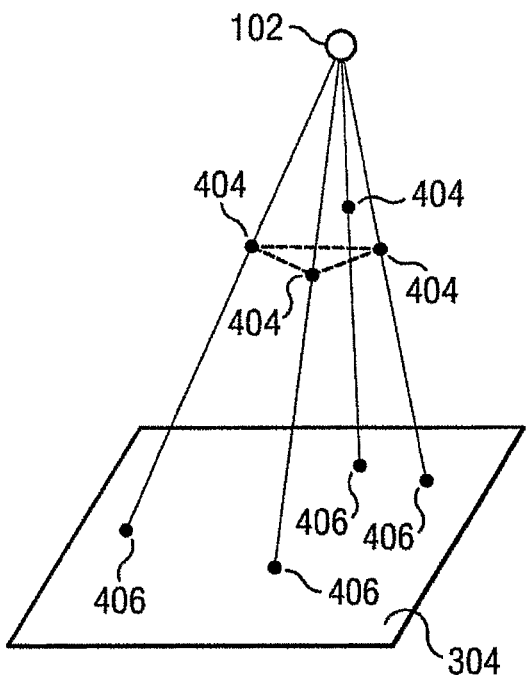
FIG. 4F is another schematic diagram illustrating the model of the fiducials in 3-D space shown in FIG. 4E, in accordance with the present disclosure.
Figure 4G:
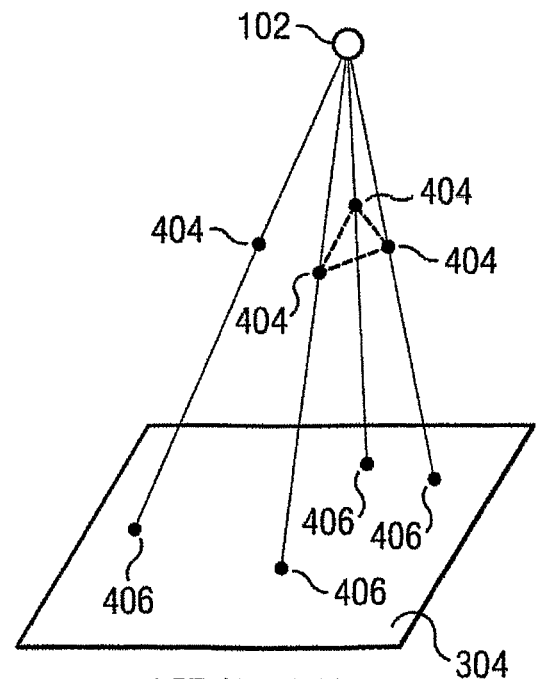
FIG. 4G is a schematic diagram illustrating another model of the fiducials in 3-D space, in accordance with the present disclosure.

To better expedite the modeling process, the involvement of a person to select a correct model as discussed above may be reduced or eliminated according the approaches disclosed with respect to FIGS. 4F and 4G. Generally, the above discussed mathematical model may be modified to include the consideration of additional fiducials. According to the illustrated approach, an extra fiducial 404 is used such that there are four fiducials 404 used instead of three, and as a result, four different three-sided pyramids may be constructed based on four different sets of triplet shadow points 406. For each three-sided pyramid, several solutions may be available. In one embodiment, the different solutions may be compared to each other, and a final solution may be chosen according to a mathematical measure known in the art. For example, the solution that has the smallest deviation from other solutions may be chosen to determine the 3-D positions of the fiducials 404 with respect to the roentgenogram 304. In another example, an average of all the solutions may be chosen to determine the 3-D positions of the fiducials 404.

The above discussed approaches may be repeated for determining 3-D positions of the fiducials 404 with respect to the other roentgenogram 302. By do so, the 3-D positions of the fiducials 404 may be determined with respect to two different coordinate systems according to the above approach. Moreover, by aligning the fiducials in the two coordinate systems, the translation and rotational orientation (x, y, z, α, β, γ) of the first and second roentgenograms may be determined in a single, fixed reference frame as illustrated in FIG. 4D. In some embodiments, by determining the 3-D positions of the fiducials 404 in a fixed reference frame, and given the predetermined relative orientation of the fiducials 404 to the object in 3-D space, the 3-D position of the object may now be determined in the fixed reference frame.

It is to be appreciated that while the above exemplary approaches may be implemented using three or four fiducials 404 to provide an efficient and precise method of accounting for the translation and rotational orientation (x, y, z, α, β, γ) of the first roentgenogram 302 relative to the second roentgenogram 304, other numbers of the fiducials 404 may be used in other approaches in accordance with the principle of the present disclosure. To allow for greater accuracy and/or precision, five or more fiducials may be used. For example, eight fiducials may be used in an embodiment as shown in FIG. 4C. In such a case, there may be 56 combinations of fiducial triplets. With at least two possible solutions for each combination, there may be at least 112 different possible solutions for the positions of the fiducials 404. A final solution may be chosen according to the following exemplary algorithm, which is based on a mathematical analysis of all the possible positions of the fiducials 404:

1) Determine all the potential 3-D positions of each fiducial 404 based on all the possible solutions obtained as discussed above 2) Determine the mean 3-D positions of each fiducial 404

3) Determine the deviations of all potential 3-D positions of each fiducial 404 from the respective mean 3-D position determined in step 2

4) Identify a least likely 3-D position corresponding to the 3-D position that deviates the most from the respective mean 3-D position determined in step 2

5) Eliminate the solution that resulted the least likely 3-D position

6) Repeat steps 1-5 until the deviation of each remaining potential 3-D position of the fiducials 404 has a deviation from the respective mean 3-D position is less than a criterion (e.g., 2 mm, 5 mm, 10 mm, etc.)

7) Approximate the 3-D position of each fiducial 404 to be the mean of each remaining potential 3-D position of the fiducials 404

It is to be appreciated that the above algorithm allows an accurate approximation for the positions of the fiducials 404, and it may be modified in accordance to the principles discussed herein and any mathematical technique known in the art. For example, in an exemplary embodiment, the algorithm may be modified to further include determining the variance between the possible positions of each fiducial 404 and eliminate potential solutions based on deviations from both the mean and variance.

Figure 5A:
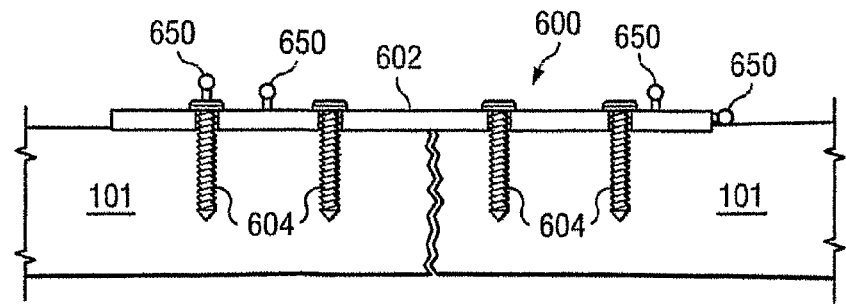
FIG. 5A a perspective view of an embodiment of a first orthopedic device comprising a plurality of fiducials, in accordance with the present disclosure.
Figure 5B:
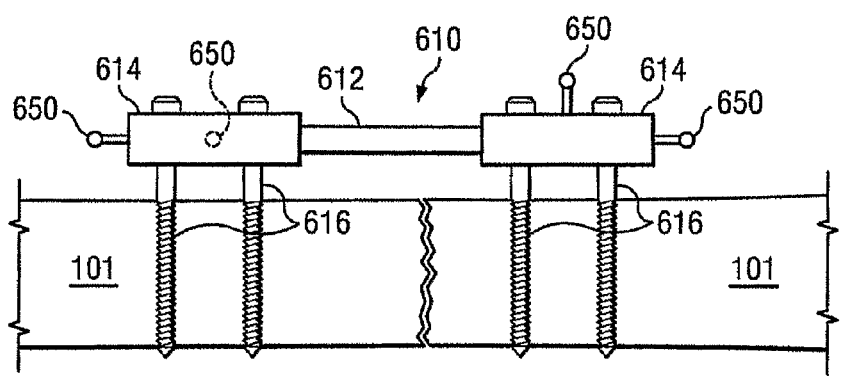
FIG. 5B a perspective view of an embodiment of a second orthopedic device comprising a plurality of fiducials, in accordance with the present disclosure.

Discussed above is an exemplary approach of using the at least one object marker 402 and fiducials 404 to create a model of objects 101 in a fixed reference frame even when the angular displacement α between two imaging orientations (120, 150) were not measured or pre-determined. In some embodiments, the object 101 and at least one object marker may be coupled to an orthopedic device, and the device can be imaged along with the object 101 for modeling the orientation of the device in 3-D space. The device may be any type of fixtures, preferably, those operable to provide structural support for the object 101, and FIGS. 5A-E illustrate several exemplary embodiments of the device. Shown in FIG. 5A is a bone plate 600 comprising a body 602 and at least one screw 604 for attachment to the object 101. The body 602 may further comprise object markers 650 disposed at an end portion and/or top portion of the body 602. Object markers 650 may also be disposed on the head of one or more screws 604 as shown in FIG. 5A. The object markers 650 may be any object marker described in the present disclosure or known in the art, and may be include a suitable number fiducials (not shown) for determining a 3-D model of the object 101 in accordance with the present disclosure. In an alternative embodiment, the bone plate 600 may serve as an object marker, and a physician may manually determine the outline of the bone plate 600 in a roentgenogram. Shown in FIG. 5B is a monolateral external fixator 610 comprising a rigid or telescopic body 612, whose length may be adjustable, and pin fixation clamps 614. The body 612 may be attached to the object 101 using a plurality of pins 616. The body 612 may further include markers 650 to indicate the dimensions of the body 612 and/or to define the orientation of the body 612 as discussed with reference to FIG. 5A. In an exemplary embodiment, the markers 650 include a suitable number fiducials (not shown) for determining a 3-D model of the object 101 in accordance with the present disclosure. In an embodiment, the markers 650 include four fiducials in total. In an alternative embodiment, the monolateral external fixator 610 may serve as an object marker, and a physician may manually determine the outline of the monolateral external fixator 610 in a roentgenogram.

Figure 5C:
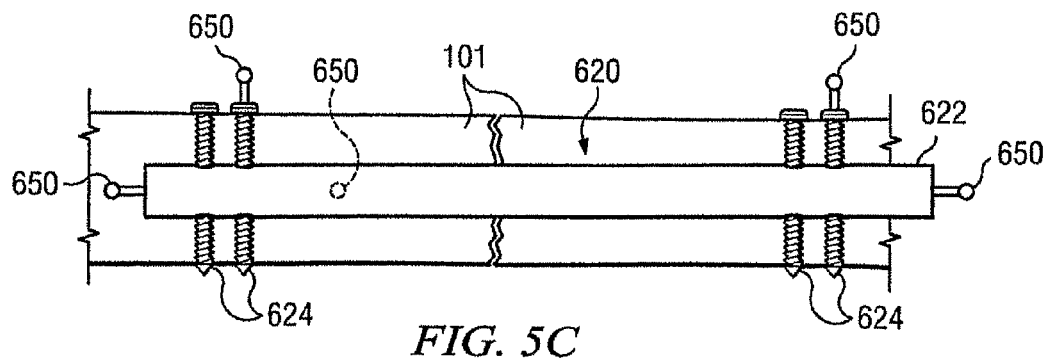
FIG. 5C a perspective view of an embodiment of a third orthopedic device comprising a plurality of fiducials, in accordance with the present disclosure.

FIG. 5C illustrates a fixture 620 similar to an intramedullary nail used in orthopedic applications. The device 620 comprises a body 622 operable to be disposed substantially within the object 101. The body 622 may be coupled to the object 101 using screws 624. The body 622 may include markers 650 that include a suitable number of fiducials (not shown) for determining a 3-D model of the object 101 in accordance with the present disclosure. In an embodiment, the markers 650 include four fiducials in total. In an alternative embodiment, the fixture 620 may serve as an object marker, and a physician may manually determine the outline of the fixture 620 in a roentgenogram.

Figure 5D:
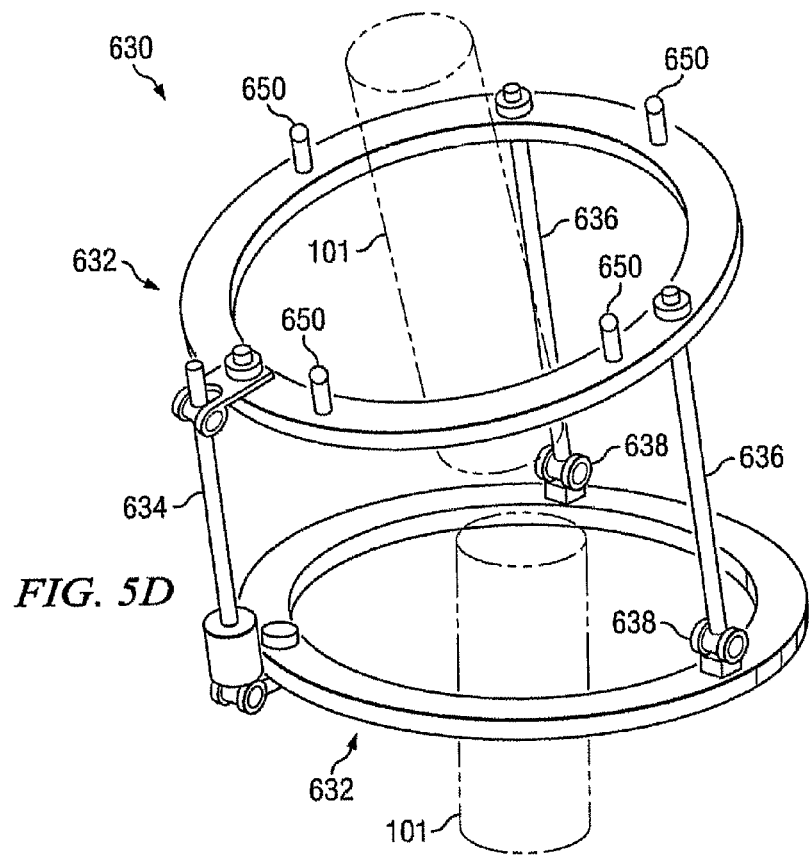
FIG. 5D a perspective view of an embodiment of a fourth orthopedic device comprising a plurality of fiducials, in accordance with the present disclosure.

FIG. 5D illustrates a circular fixator 630 similar to the TRUE/LOK device described in U.S. Pat. No. 5,681,309, which is incorporated by reference herein. The device 630 comprises at least two rings. The rings 632 are connected by two threaded rods 636 and one adjustable arm 634. The object 101 may be coupled to the rings 632, which can apply a variety of forces on the object 101. The threaded rods 636 each comprise a hinge 638 operable to provide angular adjustments while the adjustable arm 634 is operable to provide translational adjustments. The rings 632 may comprise markers 650 to define the orientation of the fixture 630 as discussed with reference to FIG. 5A. In one embodiment, four markers 650 are disposed diametrically on one of the rings 632. As such, the four markers 650 may be used to define the circular outline of the ring 632 in a roentgenogram and the center of the ring 632. The position of the center of the other ring 632 may be determined based on the known configuration of the adjustable arm 634 and the threaded rods 636. In an exemplary embodiment, the markers 650 include a suitable number fiducials (not shown) for determining a 3-D model of the object 101 in accordance with the present disclosure. In an alternative embodiment, the circular fixator 630 may serve as an object marker, and a physician may manually determine the outline of the fixator 630 in a roentgenogram.

Figure 5E:
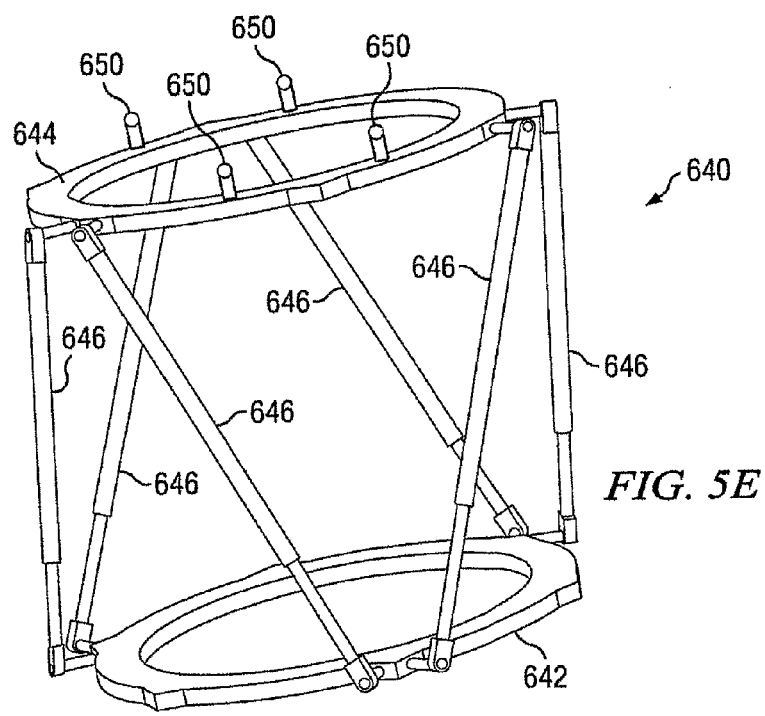
FIG. 5E a perspective view of an embodiment of a fifth orthopedic device comprising a plurality of fiducials, in accordance with the present disclosure.

FIG. 5E illustrates a hexapod-type fixture 640, which comprises first and second rings 642 and 644 of first and second dimensions and a plurality of struts 646. In the embodiment shown in FIG. 5E, the first and second rings 642 and 644 are identical fixator rings. In some embodiments, depending on the specific applications, rings of other shapes and sizes can be used in accordance with the principles disclosed herein. In some embodiments, the first and/or second rings (642, 644) may comprise markers 650 to define the orientation of the first and second rings (642, 644) as discussed with reference to FIG. 5D. In an exemplary embodiment, the markers 650 include a suitable number fiducials (not shown) for determining a 3-D model of the object 101 in accordance with the present disclosure. In an alternative embodiment, the fixture 640 may serve as an object marker, and a physician may manually determine the outline of the fixture 640 in a roentgenogram.

It is to be appreciated that the embodiments illustrated in FIGS. 5A-E are merely exemplary, and they can be modified according to various design factors disclosed herein or known in the art. It is to be further appreciated that in some embodiments, an object marker may not include a fiducial. In an exemplary embodiment, an orthopedic device coupled to the object 101 may be used as an object marker. After the orthopedic device is imaged in the roentgenograms together with the object 101, the outline of the orthopedic device may be determined either manually or using a suitable graphic software. For example, a physician may manually outline the orthopedic device and input such information into a computer. In another embodiment, the outline of the orthopedic device may be automatically generated by pattern recognition software. The outline of the orthopedic device may, in turn, be used to for determining a 3-D model of the object 101 in accordance with the present disclosure as discussed with respect to FIGS. 5A-E.

As illustrated with respect to FIGS. 4 and 5, the above described approach is directed to using the predetermined positions of the fiducials 404 relative to each other to create a model of objects 101 in a fixed frame. It to be appreciated, however, other approaches may be used to create a model of objects 101 in a fixed frame without predetermining or using the positions of the fiducials 404 relative to each other. According to another exemplary approach of using object markers 402 and fiducials 404 to create a model of objects 101 in a fixed frame, two roentgenograms (302, 304) are prepared of the objects 101 at different relative orientations (120, 150). Each of these roentgenograms (302, 304) includes an image of the objects 101 and an image at least one reference marker (e.g., 106, 107) having at least two fiducials (e.g., 122, 124, 132, 138, 140, 142). In addition, the roentgenograms (302, 304) also include an image of at least one object marker 402 attached to the objects 101.

Figure 6B:
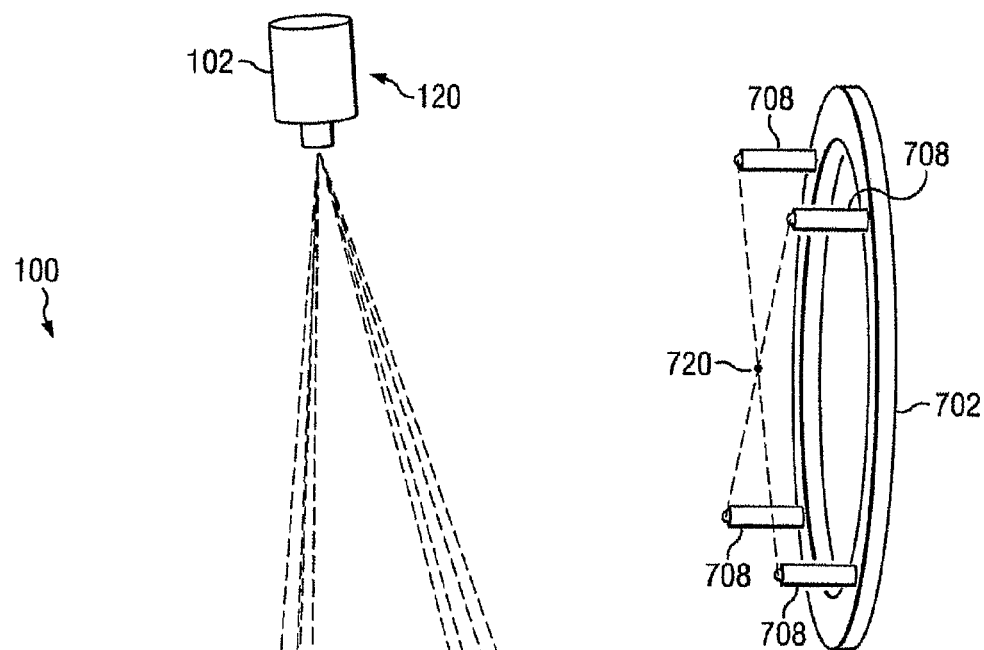
FIG. 6B is a partial, focused view of the orthopedic device shown in FIG. 6A, in accordance with the present disclosure.
Figure 6A:
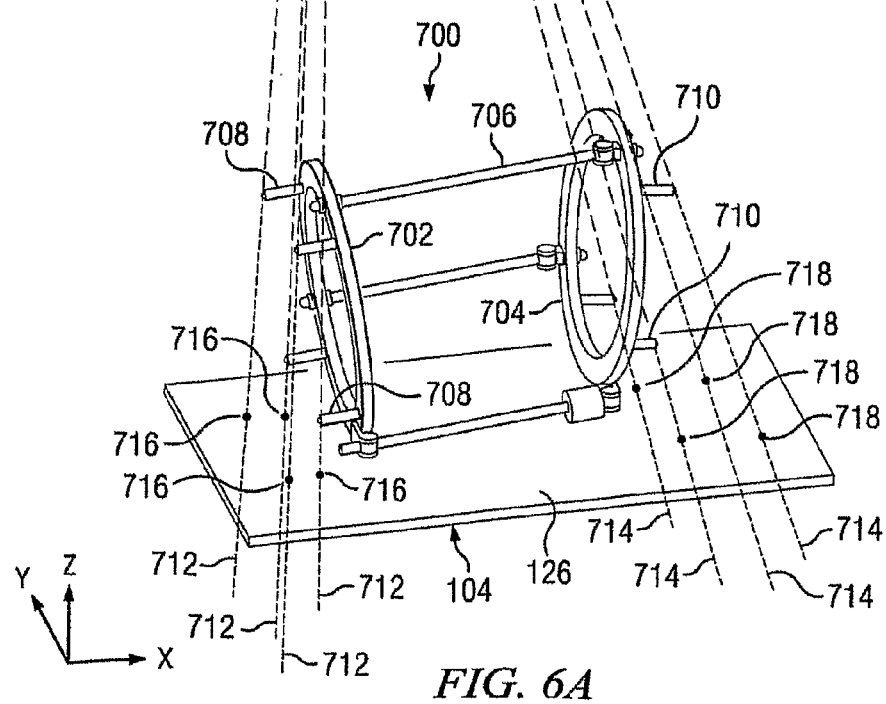
FIG. 6A is a schematic diagram illustrating an orthopedic device being imaged, in accordance with the present disclosure.

Turning now to FIG. 6A in an exemplary embodiment, the object 101 is coupled to an external fixator 700, which may be similar to the device 630 of FIG. 5D, and further includes first and second plurality of object markers 708 and 710 coupled to the first and second rings 702 and 704, respectively. Each marker of the first and second plurality of object markers 708 and 710 may have the same height. In the illustrated embodiment, the fixator 700 has a pair of rings 702 and 704 each having a known radius, and the first plurality of object markers 708 comprise four markers 708 disposed diametrically on an outward surface of the ring 702. In some embodiments, the object markers 708 may be mounted on a top, bottom, exterior, or interior surface of the ring 702. In some other embodiments, the object markers 708 may be portions of the device 700 that are defined at diametric positions. According to an embodiment, the ring 702 may be made of a material that is substantially translucent to short-wavelength radiation, and the object markers 708 may be partially disposed or completely embedded inside the ring 702. According to another embodiment, the ring 702 may be made of a radio opaque material and include holes defined therethrough that correspond to the object markers 708. It is to be appreciated that the various embodiments of the ring 702 and markers 708 may be implemented with respect to the ring 704 and markers 710 in accordance with the principles of the present disclosure.

FIG. 6B is an exploded view of the object markers 708, along with two imaginary lines drawn through the tips of the diametrically opposing object markers 708, thereby defining a first reference point 720 proximate to the first ring 702 at the point at which the two imaginary lines cross. The first reference point 720 has a predefined spatial relationship with the first ring 702 and thus a fixed relationship with the imaged object. In the case of the illustrated embodiment, the first reference point 720 is spaced from the center of ring 702 by a distance equal to the height of the object marker 708.

Turning back to FIG. 6A, the second plurality of object markers 710 similarly comprise four markers 710 disposed diametrically on an outward surface of the ring 704. Two imaginary lines (not shown) can be drawn through the tips of the diametrically opposing object markers 710, thereby defining a second reference point 722 (not shown) proximate to the second ring 704 at the point at which the two imaginary lines cross. The second reference point has a predefined spatial relationship with the second ring, and in the case of the illustrated embodiment, the second reference point is spaced from the center of ring 704 by a distance equal to the height of the object marker 710.

To model the orientation of the device 700 in 3-D space, two roentgenograms of the device 700 are taken using the imaging system 100. First, as illustrated in FIG. 6A, the adjustable fixator 700 is disposed in the first path between the x-ray source 102 and the imager 104, and the adjustable fixator 700, the x-ray source 102, and the imager 104 are in a first orientation 120 relative to each other. The first path includes x-ray trajectories represented by lines 712 and 714, which pass through the tips of the object markers 708 and 710, respectively. A first roentgenogram of the adjustable device 700 is generated when x-rays are directed from the x-ray source 102 along the first path toward the device 700 in the first path. As such, the first roentgenogram includes a projection of the first and second plurality of markers in the first plane 126, including projection points 716 and 718 that correspond to the tips of the object markers 708 and 710, respectively.

Figure 7:
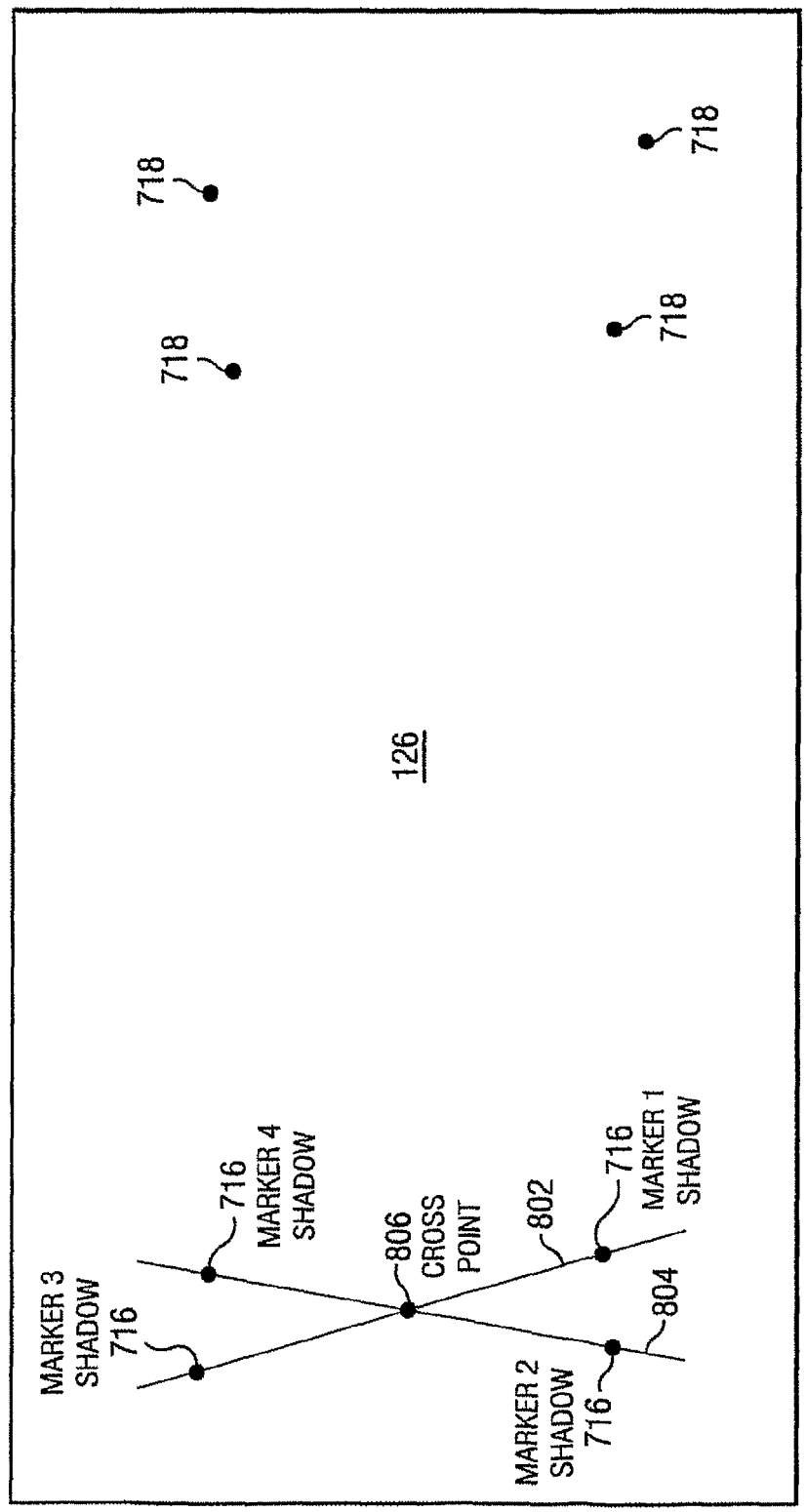
FIG. 7 is a schematic diagram illustrating a roentgenogram including images of a plurality of fiducials, in accordance with the present disclosure.

Shown in FIG. 7 are the projection points 716 as projected in the first plane 126 as discussed above. Two lines 802 and 804 are drawn through the projection points 716 of the diametrically opposing object markers 708. The lines 802 and 804 intersect at a cross point 806, which corresponds to the projection of the first reference point 720 in the first plane 126. Given coordinates of the projection points 716, the three dimensional coordinates of the cross point 806 may be mathematically determined using known algebraic and trigonometric techniques.

Figure 8:
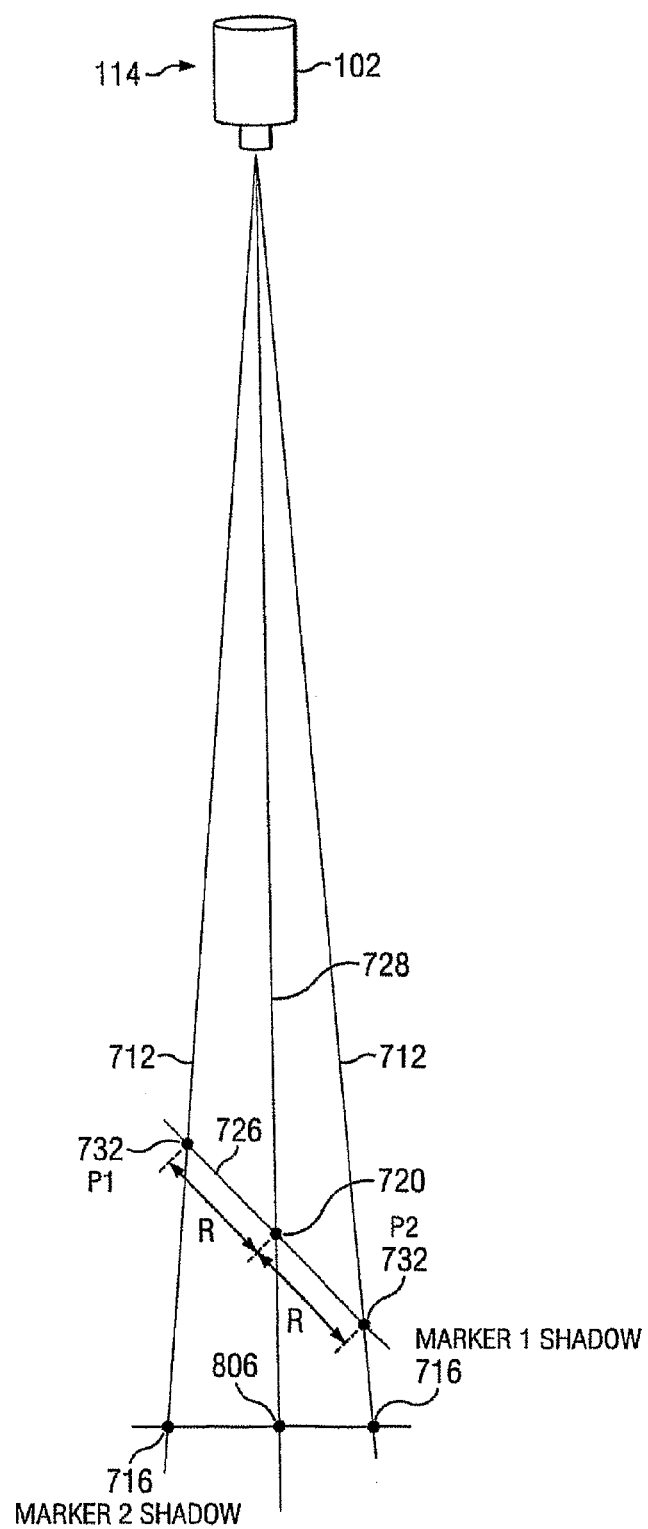
FIG. 8 is a schematic diagram illustrating a mathematical model of the fiducials shown in FIG. 7, in accordance with the present disclosure.

FIG. 8 is a schematic illustration of the cross point 806 and projection points 716 of a pair of diametrically opposing object markers 708 in the first 3-D coordinate system 128 defined as discussed above. The coordinates of the x-ray source 102 in the first orientation 114 have been determined through the use of markers 106 as discussed above. As such, the 3-D trajectories 712 and 728 of the x-rays from the x-ray source 102 can be traced by connecting the x-ray source 102 and the projection points 716 and 806. The first reference point 720 is located somewhere along trajectory 728, which connects the x-ray source 102 and the crossed point 806. To determine the location of the first reference point 720 in the first 3-D coordinate system 128, an iterative process may used to determine a line 726 that intersects trajectories 728 and 712 at points 732 and the first reference point 720 such that the distance between each point 732 and the first reference point 720 is equal to the radius of the ring 702. Given the known radius of the ring 702 and the orientation of the line 726 along with coordinates of the x-ray source 102, the projection points 716, and the cross point 806, the coordinate of the first reference point 720 may be mathematically determined using known triangulation and trigonometric techniques.

As such, the orientation of the first ring 702 can be determined based on the defined spatial relationship between first reference point 720 and the first ring 702. In particular, the position of the center of the first ring 702 may be determined from the location of the first reference point 720. Although FIG. 8 only depicts the use of two projection points 716, along with a single cross point 806, these calculations can be made with four, six, or more projection points, thereby improving the accuracy of the 3-D model of the rings.

To create a model of objects 101 in a fixed frame using the fixture 700, an embodiment may involve further determining the coordinates of the second reference point 722 and using the coordinates of the second reference point 722 to determine the position of the center of the second ring 704. The coordinates of the second reference point 722 may be determined from the coordinates of the first reference point 720 and predetermined lengths of the struts 706. It is to be appreciated that in some embodiments, such as one in which the fixture 700 comprises a hexapod, the coordinates of the second reference point of the second ring 704 and the orientation of the second ring 704 can be determined from the orientation of the first ring 702 and the length of each of the struts 706. Alternatively, the discussions above with respect to FIGS. 6-9 provide an approach of determining the coordinates of the first reference point, and same method can be applied to determine the coordinates of the second reference point 722 of the second ring 704.

As discussed above, two roentgenograms of the fixture 700 are prepared. The above discussed method described with respect to FIGS. 6-8 may be repeated to determined coordinates of the first and second reference points 720 and 722 and the centers of the first and second rings 702 and 704 with respect to a second roentgenogram. The centers of the rings 702 and 704 define an arbitrary line in each roentgenogram, and by aligning the arbitrary line in a fixed frame, the roentgenograms may then be aligned at angles α to create a model of objects 101 in a fixed reference frame as discussed above. Moreover, the roentgenograms may be orientated at angles β and γ creating various test 3-D models of the imaged objects 101 by aligning roentgenograms (302, 304) at various angle β and γ, and finally identifying a 3-D model that would produce 2-D projections that substantially match the outlines of the imaged object 101 in the first and second roentgenogram 302 and 304. The test models of the objects 101 may be created according to the approach described above with respect to FIGS. 3C-G to provide better accuracy. It is to be appreciated, however, that the various test models may be generated according to any suitable modeling technique known in the art.

Figure 9:
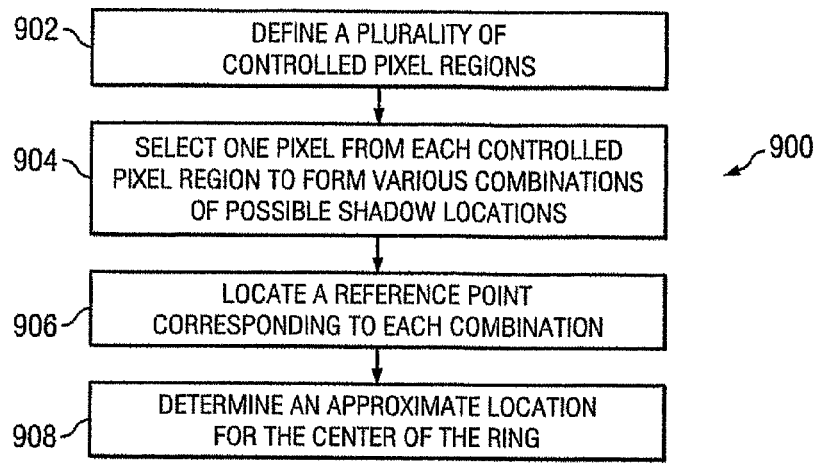
FIG. 9 is a flow diagram illustrating an exemplary algorithm, in accordance with the present disclosure.

It is to be appreciated that in some embodiments, a visible shadow may span across more than one pixel on a digital roentgenogram. Accordingly, the precise location of the visible shadow may be approximated using an approximation model. FIG. 9 is a flow chart illustrating the approach of one exemplary approximation model 900. The approximation model 900 includes a step 902 for defining a plurality of controlled pixel regions each comprising a plurality of pixels. The plurality of pixels of each controlled pixel region may correspond to the locations at which each visible shadow is most likely to be located. For example, a defined controlled pixel region may include a 3×3 grid of nine pixels around a visible shadow. In another example, a defined controlled pixel region may include a 4×4 grid of 16 pixels around a visible shadow. The exemplary model 900 may include a step 904 for arbitrarily assigning multiple combinations of possible shadow locations based on different sets of pixels, each set of pixels comprising one pixel from each defined controlled pixel region. The exemplary model 900 may include a step 906 for determining a location for a desired reference point for each assigned combination of shadow locations. For example, the desired reference point may be the center of the ring 702 or the first reference point 720 discussed with respect to FIGS. 6-8. In an embodiment, all combinations of shadow locations are assigned and used to determine a location for the desired reference point. In another embodiment, only selected combinations of shadow locations are assigned and used to determine a location for the desired reference point. The exemplary model 900 may further include a step 908 for processing the first and second locations of the desired reference point using an objective criterion to determine an approximated location for the center of the ring. In an exemplary embodiment, the objective criterion of step 908 may include one or more mathematics measurement known in the art, such mean, median, variance, standard deviation, or any combination thereof. In an exemplary embodiment, locations with differences of more than 0.01 mm may all be filtered out. In cases when none of the combinations of chosen regions provides that precision, the combination with the least difference in ring center positioning may be used.

Figure 10:
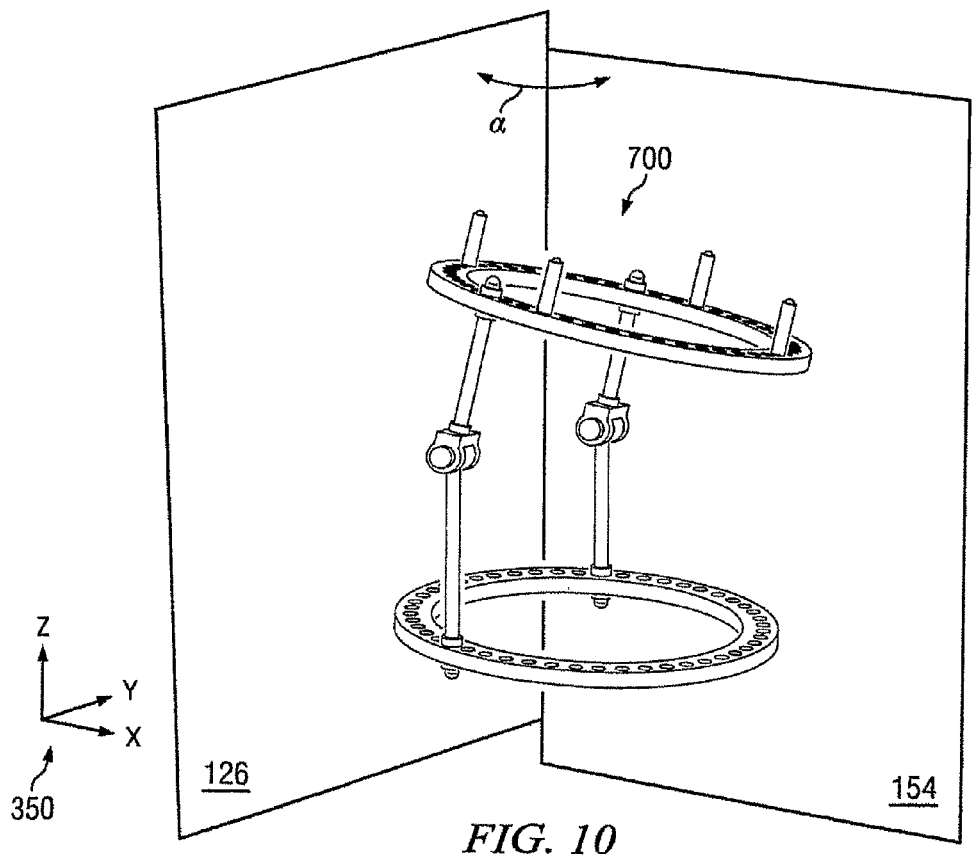
FIG. 10 is a schematic diagram illustrating an imaged object in a 3-D framework, in accordance with the present disclosure.

FIG. 10 is a schematic diagram showing a model of the fixture 700 in a combined 3-D coordinate system 350. As discussed above with respect to FIGS. 2A-C, first and second 3-D coordinate systems are individually created based on two roentgenograms and comprise first and second planes 126 and 154, respectively. The first and second 3-D coordinate systems 128 and 158 are combined to create the combined 3-D coordinate system 350. The first and second planes 126 and 154 are aligned at an angle α such that the coordinates of the first and second reference points in the first and second 3-D coordinate systems coincide.

Figure 11:
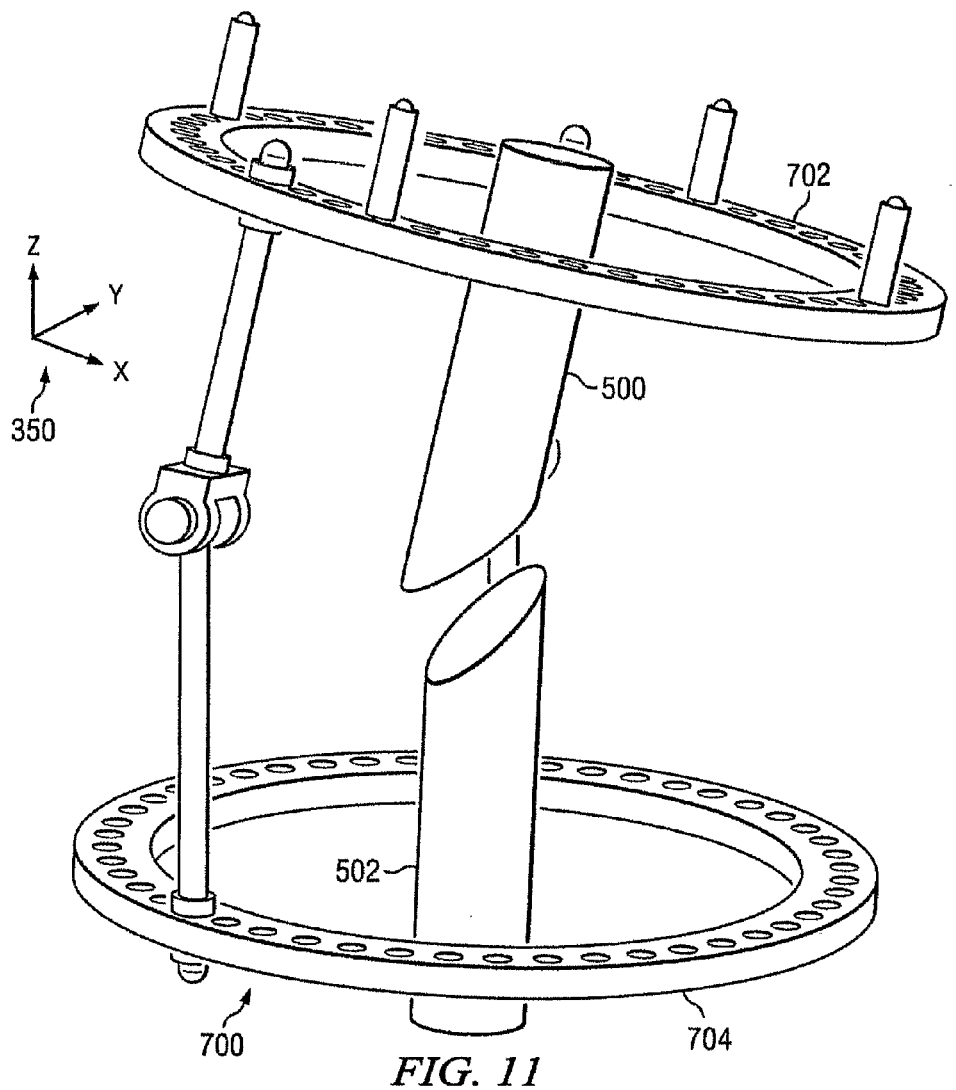
FIG. 11 is a schematic diagram illustrating an exemplary 3-D model of an object.

FIG. 11 is a model of a first object segment 500 coupled to the first ring 702 of the fixture 700 and a second object segment 502 coupled to the second ring 704 of the fixture 700. The model is based on the combined 3-D coordinate system 350 generated using the method discussed above. In some embodiments, the model of FIG. 10 allows for the determination of the orientation of the first bone segment 500 relative to the orientation of the second segment 502. In particular, the model allows for mathematically determining the relative orientation of the first and second bone segments 500 and 502 based on various orientations of the first ring 702 relative to the second ring 704.

This disclosure has described using two imaging orientations that are substantially orthogonal with respect to each other or non-orthogonal orientations. The choice between these two embodiments may depend upon a variety of factors, including equipment limitations and interest or lack of interest in the imaging certain orientations. Furthermore, more than two imaging orientations may be utilized consistent with the scope of the present disclosure. By using more than two imaging orientations, the accuracy of the 3-D model of the frame and the tissue can be improved.

Once a 3-D model of the frame and the tissue segments has been created, a physician or surgeon can more readily understand the nature of the fracture and the degree of fixation, compression, or distraction (or other force) that should be applied to the tissue segments in order to achieve the desired result. It is contemplated that the 3-D model of a hexapod ring fixator can be coupled with an automated frame controller such that the desired fixation, compression, or distraction commands can be automatically implemented.

Figure 12:
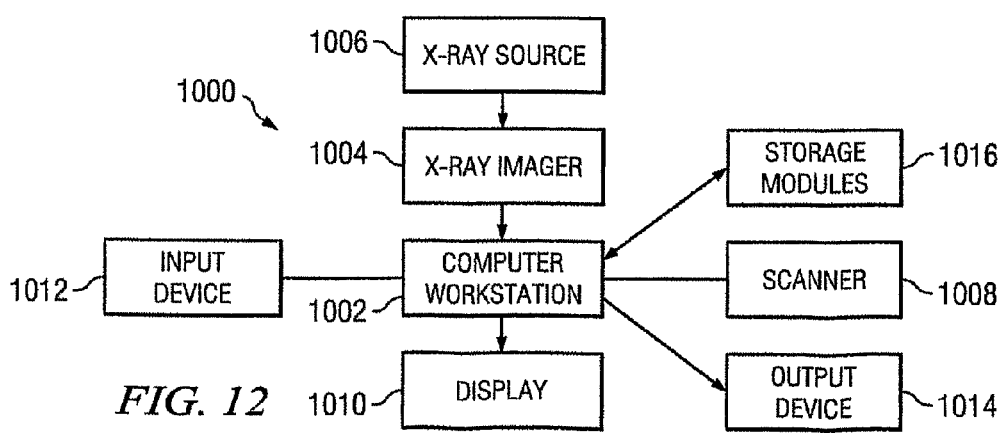
FIG. 12 is a schematic block diagram illustrating an exemplary system for creating 3-D model of an object.

As discussed above, a 3-D model of an object may be generated from roentgenograms of the object. FIG. 12 is a schematic diagram of a system 1000 operable to digitally generate a 3-D model of an imaged object (not shown) in accordance with the principles of the present disclosure. The system 1000 may include a computer workstation 1002 operable to receive roentgenograms of the imaged object, and the computer workstation 1002 may include one or more microprocessors/controllers in communication with a variety of auxiliary devices. In an embodiment, the system 1000 may include an x-ray imager 1004 in communication with the computer workstation 1002, and the x-ray imager 1004 is operable to receive x-ray light from an x-ray source 1006 passing through the imaged object. The x-ray imager 1004 may be operable to generate a roentgenogram directly, or it may be operable to transmit image data to the computer workstation 1002, which may then generate the x-ray image. In another embodiment, the system 1000 may include a scanner 1008 in communication with the workstation 1002, and the scanner 1008 may be operable to scan an x-ray film into digitized roentgenogram. In some embodiments, the system 1000 may further include a display 1010 in communication with the workstation 1002, and the display 1010 may be a LCD display, a CRT display, or any other displaying device known in the art. The workstation 1002 may be configured to display the digitized roentgenogram to a user on the display 1010, and the user may input a variety of data pertaining to the displayed roentgenogram as in the present disclosure, such as the location of fiducials, the predetermined position of the fiducials relative to each other. In an exemplary embodiment, the system 1000 includes one or more input device 1012, such as a mouse, lightpen and/or keyboard, in communication with the workstation 1002, and the user may input the data using the input device 1012. Based on the user-input data and image data, the microprocessor or controller of the workstation 1002 may generate a 3-D model of the imaged object in accordance with the present disclosure. In some embodiments, the system 1000 may further include an output device 1014, such as a printer, operable to provide various model data, calculation results, images, or graphics to the user. The system 1000 may further include a storage module 1016 for storing various model data, calculation results, images, or graphics for later use.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

While the methods and systems of this invention have been described in terms of preferred embodiments, it will be apparent to those of skill in the art that variations may be applied to the methods and systems and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A method of transforming a plurality of roentgenograms of an object into a 3-D model of the object using a data transformation server, the method comprising:

receiving, using one or more processing devices of the data transformation server and from an x-ray imager, a first roentgenogram of an object disposed between an x-ray source and the x-ray imager in a first orientation, wherein the first roentgenogram is generated using the x-ray imager, wherein the first orientation comprises a first angular position of the object relative to an imaging axis, wherein the first roentgenogram includes a first image of:
the object; and
at least one reference marker having at least two fiducials, wherein the fiducials are separated by a fixed distance;

receiving, using the one or more processing devices and from the x-ray imager, a second roentgenogram of the object disposed between the x-ray source and the x-ray imager in a second orientation, wherein the second roentgenogram is generated using the x-ray imager, wherein the second orientation comprises a second angular position of the object relative to the imaging axis, and wherein the second roentgenogram includes a second image of:
the object; and
the at least one reference marker;

receiving, using the one or more processing devices and from the x-ray imager, an angular displacement corresponding to the difference between the first and second angular positions of the object relative to the imaging axis;

determining, using the one or more processing devices, a first 3-D position of the x-ray source with respect to the x-ray imager in the first orientation using the first image of the at least one reference marker;

determining, using the one or more processing devices, a second 3-D position of the x-ray source with respect to the x-ray imager in the second orientation using the second image of the at least one reference marker;

identifying, using the one or more processing devices, a first object outline of the imaged object in the first roentgenogram;

identifying, using the one or more processing devices, a second object outline of the imaged object in the second roentgenogram;

generating, using the one or more processing devices, a first 3-D object projection from the first outline of the imaged object to the first 3-D position of the x-ray source;

generating, using the one or more processing devices, a second 3-D object projection from the second outline of the imaged object to the second 3-D position of the x-ray source;

aligning, using the one or more processing devices, the first and second 3-D projections of the imaged object in a 3-D reference frame using the angular displacement; and transforming, using the one or more processing devices, the first and second 3-D object projections into a 3-D model of the imaged object in the 3-D reference frame.

2. The method according to claim 1, the method further comprising:

identifying, using the one or more processing devices, a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation;

identifying, using the one or more processing devices, one or more intersection planes passing through the tilt axis and through the first and second 3-D projections of the imaged object in the 3-D reference frame;

for each of the one or more intersection planes, performing the following steps a) through c):

a) identifying, using the one or more processing devices, one or more intersection points between the first and second 3-D object projections, and said intersection plane in the 3-D reference frame;

b) generating, using the one or more processing devices, one or more polygons connecting the intersection points in said intersection plane;

c) generating, using the one or more processing devices, one or more closed curves within the each of the one or more polygons, wherein the one or more closed curves corresponds to a cross-sectional view of the imaged object in said intersection plane; and generating, using the one or more processing devices, a surface in the 3-D reference frame that connects each of the closed curves to form a 3-D model of the imaged object.

3. The method according to claim 1, wherein the at least one reference marker comprises at least three fiducials, the method further comprising:

receiving, using the one or more processing devices, a first outline of the at least three fiducials in the first roentgenogram; and receiving, using the one or more processing devices, a second outline of the at least three fiducials in the second roentgenogram;

wherein determining the first 3-D position of the x-ray source further comprises identifying a first plurality of paths from the x-ray source to the first outline of the at least three fiducials and determining an approximate intersection of the first plurality of light paths; and wherein determining the second 3-D position of the x-ray source further comprises identifying a second plurality of paths from the x-ray source to the second outline of the at least three fiducials and determining an approximate intersection of the second plurality of light paths.

4. The method according to claim 3, wherein determining the approximate intersection of the first plurality of paths and the approximate intersection of the second plurality of paths further comprises using an approximation model.

5. The method according to claim 4, wherein using an approximation model further comprises determining the position of a first segment between the first plurality of paths and designating a point on the first segment to be the first 3-D position of the x-ray source.

6. The method according to claim 5, wherein the first segment is a common perpendicular of the first plurality of paths.

7. The method according to claim 5, wherein using an approximation model further comprises determining the position of a second segment between the second plurality of paths and designating a point on the second segment to be the second 3-D position of the x-ray source.

8. The method according to claim 7, wherein the second segment is a common perpendicular of the second plurality of paths.

9. The method according to claim 1, wherein the at least one reference marker comprises at least three fiducials disposed along a longitudinal axis of the at least one reference marker.

10. The method according to claim 1, wherein the first roentgenogram includes a first image of first and second reference markers, and the second roentgenogram includes a second image of the first and second reference markers.

11. The method according to claim 10, wherein the first reference marker comprises two fiducials disposed along a longitudinal axis of the first reference marker, and the second reference marker comprises two fiducials disposed along a longitudinal axis of the second reference marker.

12. The method according to claim 10, wherein the first reference marker comprises two fiducials disposed along a longitudinal axis of the first reference marker, and the second reference marker comprises first, second, and third fiducials, wherein first and second fiducials of the second reference marker define a first longitudinal axis parallel to the x-ray imager, and the second and third fiducials of the second reference marker define a second longitudinal axis orthogonal to the first longitudinal axis.

13. The method according to claim 1, wherein receiving an angular displacement further comprises receiving data from a measuring device coupled to the object or the imaging device, the measuring device being operable to determine the angular displacement.

14. The method according to claim 1, wherein the at least one reference marker is made of a radio-translucent material and the fiducials of the at least one reference marker are made of a radio-opaque material.

15. A method of transforming a plurality of roentgenograms of an object into a 3-D model of the object using a data transformation server, the method comprising:

receiving, using one or more processing devices of the data transformation server and from an x-ray imager, a first roentgenogram of an object disposed between an x-ray source and the x-ray imager in a first orientation, wherein the first roentgenogram is generated using the x-ray imager, wherein the first orientation comprises a first angular position of the object with respect to an imaging axis, wherein the imaging axis is parallel to the imager in the first orientation, wherein the first roentgenogram includes a first image of:

the object; and at least one reference marker having at least two fiducials, wherein the fiducials are separated by a fixed distance;

receiving, using the one or more processing devices and from the x-ray imager, a second roentgenogram of the object disposed between the x-ray source and the x-ray imager in a second orientation, wherein the second roentgenogram is generated using the x-ray imager, wherein the second orientation comprises a second angular position of the object with respect to the imaging axis, wherein the imaging axis is parallel to the imager in the second orientation and the second angular position of the object is orthogonal to the first angular position of the object, and further wherein the second roentgenogram includes a second image of:

the object; and the at least one reference marker;

determining, using the one or more processing devices, a first 3-D position of the x-ray source with respect to the x-ray imager in the first orientation using the first image of the at least one reference marker;

determining, using the one or more processing devices, a second 3-D position of the x-ray source with respect to the x-ray imager in the second orientation using the second image of the at least one reference marker;

identifying, using the one or more processing devices, a first object outline of the imaged object in the first roentgenogram;

identifying, using the one or more processing devices, a second object outline of the imaged object in the second roentgenogram;

generating, using the one or more processing devices a first 3-D object projection from the first outline of the imaged object to the first 3-D position of the x-ray source;

generating, using the one or more processing devices, a second 3-D object projection from the second outline of the imaged object to the second 3-D position of the x-ray source;

aligning, using the one or more processing devices, the first and second 3-D projections of the imaged object in a 3-D reference frame according to the orthogonal first and second angular positions of the object; and transforming, using the one or more processing devices, the first and second 3-D object projections into a 3-D model of the imaged object in the 3-D reference frame.

16. The method according to claim 15, the method further comprising:

identifying, using the one or more processing devices, a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation;

identifying, using the one or more processing devices, one or more intersection planes passing through the tilt axis and through the first and second 3-D projections of the imaged object in the 3-D reference frame;

for each of the one or more intersection planes, performing the following steps a) through c):

a) identifying, using the one or more processing devices, one or more intersection points between the first and second 3-D object projections, and said intersection plane in the 3-D reference frame;

b) generating, using the one or more processing devices, one or more polygons connecting the intersection points in said intersection plane;

c) generating, using the one or more processing devices, one or more closed curves within the each of the one or more polygons, wherein the one or more closed curves corresponds to a cross-sectional view of the imaged object in said intersection plane; and generating, using the one or more processing devices, a surface in the 3-D reference frame that connects each of the closed curves to form a 3-D model of the imaged object.

17. The method according to claim 15, wherein the at least one reference marker comprises at least three fiducials in total, the method further comprising:

receiving, using the one or more processing devices, a first outline of the at least three fiducials in the first roentgenogram; and receiving, using the one or more processing devices, a second outline of the at least three fiducials in the second roentgenogram;

wherein determining the first 3-D position of the x-ray source further comprises identifying a first plurality of paths from the x-ray source to the first outline of the least three fiducials and determining an approximate intersection of the first plurality of paths; and wherein determining the second 3-D position of the x-ray source further comprises identifying a second plurality of paths from the x-ray source to the first outline of the least three fiducials and determining an approximate intersection of the second plurality of paths.

18. A method transforming a plurality of roentgenograms of an object into a 3-D model of the object using a data transformation server, the method comprising:

receiving, using one or more processing devices of the data transformation server and from an x-ray imager, a first roentgenogram of an object disposed between an x-ray source and the x-ray imager in a first orientation, wherein the first roentgenogram is generated by the x-ray imager, wherein the first orientation comprises a first angular position of the object relative to an imaging axis, wherein the first roentgenogram includes a first image of:

the object;

at least one reference marker having at least two fiducials, wherein the fiducials are separated by a fixed distance; and at least one object marker attached to the object, wherein the object marker includes at least one fiducial of fixed dimensions;

receiving, using the one or more processing devices and from the x-ray imager, a second roentgenogram of the object disposed between the x-ray source and the x-ray imager in a second orientation, wherein the second roentgenogram is generated by the x-ray imager, wherein the second orientation comprises a second angular position of the object relative to the imaging axis, and wherein the second roentgenogram includes a second image of:

the object;

the at least one reference marker; and the at least one object marker;

determining, using the one or more processing devices, a first 3-D position of the x-ray source with respect to the x-ray imager in the first orientation using the first image of the at least one reference marker;

determining, using the one or more processing devices, a second 3-D position of the x-ray source with respect to the x-ray imager in the second orientation using the second image of the at least one reference marker;

generating, using the one or more processing devices, a first 3-D object marker projection from the at least one object marker in the first roentgenogram to the first 3-D position of the x-ray source;

generating, using the one or more processing devices, a second 3-D object marker projection from the at least one object marker in the second roentgenogram to the second 3-D position of the x-ray source;

aligning, using the one or more processing devices, the first and second 3-D object marker projections in a 3-D reference frame using the first and second object marker projections;

identifying, using the one or more processing devices, a first object outline of the imaged object in the first roentgenogram identifying, using the one or more processing devices, a second object outline of the imaged object in the second roentgenogram generating, using the one or more processing devices, a first 3-D object projection from the first object outline to the first 3-D position of the x-ray source;

generating, using the one or more processing devices, a second 3-D object projection from the second object outline to the second 3-D position of the x-ray source;

aligning, using the one or more processing devices, the first and second 3-D object projections in the 3-D reference frame using the alignment of the first and second 3-D object marker projections in the 3-D reference frame; and transforming, using the one or more processing devices, the first and second 3-D object projections into a 3-D model of the imaged object in the 3-D reference frame.

19. The method according to claim 18, the method further comprising:
identifying, using the one or more processing devices, a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation;
identifying, using the one or more processing devices, one or more intersection planes passing through the tilt axis and through the first and second 3-D projections of the imaged object in the 3-D reference frame;
for each of the one or more intersection planes, performing the following steps a) through c):
a) identifying, using the one or more processing devices, one or more intersection points between the first and second 3-D object projections, and said intersection plane in the 3-D reference frame;
b) generating, using the one or more processing devices, one or more polygons connecting the intersection points in said intersection plane;
c) generating, using the one or more processing devices, one or more closed curves within the each of the one or more polygons, wherein the one or more closed curves corresponds to a cross-sectional view of the imaged object in said intersection plane; and
generating, using the one or more processing devices, a surface in the 3-D reference frame that connects each of the closed curves to form a 3-D model of the imaged object.

20. The method according to claim 18, wherein the at least one object marker includes at least three fiducials, wherein the fiducials are separated by fixed distances, and further wherein:
generating the first 3-D object marker projection further comprises generating a first 3-D projection of the at least three fiducials from the object marker in the first roentgenogram to the first 3-D position of the x-ray source;
generating the second 3-D object marker projection further comprises generating a second 3-D projection of the at least three fiducials from the object marker in the second roentgenogram to the second 3-D position of the x-ray source; and
aligning the first and second 3-D object marker projections in the 3-D reference frame further comprises determining 3-D locations of the at least three fiducials in the 3-D reference frame.

21. The method according to claim 20, wherein determining the 3-D locations of the at least three fiducials further comprises:
providing a plurality of mathematical solutions that may represent the 3-D locations of the at least three fiducials; and
receiving an instruction that selects one of the plurality of mathematical solutions to be the 3-D locations of the at least three fiducials.

22. The method according to claim 18, wherein the at least one object marker includes at least four fiducials, wherein the at least four fiducials are separated by fixed distances, and further wherein:

generating the first 3-D object marker projection comprises generating a first 3-D projection of the at least four fiducials from the object marker in the first roentgenogram to the first 3-D position of the x-ray source;
generating the second 3-D object marker projection comprises generating a second 3-D projection of the at least four fiducials from the object marker in the second roentgenogram to the second 3-D position of the x-ray source; and
aligning the first and second 3-D object marker projections in the 3-D reference frame further comprises determining 3-D locations of the at least four fiducials in the 3-D reference frame.

23. The method according to claim 22, wherein determining the 3-D locations of the at least four fiducials further comprises:
providing a plurality of mathematical solutions that may represent the 3-D locations of the at least four fiducials; and
determining the 3-D locations of the at least four fiducials according to a mathematical correlation between the plurality of mathematical solutions.

24. The method according to claim 18, wherein the at least one reference marker comprises at least three fiducials, the method further comprising:
receiving, using the one or more processing devices, a first outline of the at least three fiducials in the first roentgenogram; and
receiving, using the one or more processing devices, a second outline of the at least three fiducials in the second roentgenogram;
wherein determining the first 3-D position of the x-ray source comprises identifying a first plurality of paths from the x-ray source to the first outline of the least three fiducials and determining an approximate intersection of the first plurality of paths; and
wherein determining the second 3-D position of the x-ray source comprises identifying a second plurality of paths from the x-ray source to the first outline of the least three fiducials and determining an approximate intersection of the second plurality of paths.

25. The method according to claim 24, wherein determining the approximate intersection of the first plurality of paths and the approximate intersection of the second plurality of paths comprises using an approximation model.

26. The method according to claim 25, wherein using an approximation model further comprises determining the position of a first segment between the first plurality of paths and designating a point on the first segment to be the first 3-D position of the x-ray source.

27. The method according to claim 26, wherein the first segment is a common perpendicular of the first plurality of paths.

28. The method according to claim 26, wherein using an approximation model further comprises determining the position of a second segment between the second plurality of paths and designating a point on the second segment to be the second 3-D position of the x-ray source.

29. The method according to claim 28, wherein the second segment is a common perpendicular of the second plurality of paths.

30. The method according to claim 18, wherein the at least one object marker is directly attached to the object.

31. The method according to claim 18, wherein the at least one object marker is indirectly attached to the object.

32. The method according to claim 18, wherein the at least one reference marker is made of a radio-translucent material and the fiducials of the at least one reference marker are made of a radio-opaque material.

33. The method according to claim 18, wherein the at least one object marker is made of a radio-translucent material and the fiducial of the at least one object marker is made of a radio-opaque material.

34. A method of transforming a plurality of roentgenograms of an object into a 3-D model of the object using a data transformation server, the object being coupled to at least one ring of an orthopedic fixator, the at least one ring having a predetermined diameter, the method comprising:
receiving, using one or more processing devices of the data transformation server and from an x-ray imager, a first roentgenogram of an object disposed between an x-ray source and the x-ray imager in a first orientation, wherein the first roentgenogram is generated by the x-ray imager, wherein the first orientation comprises a first angular position of the object relative to an imaging axis, wherein the first roentgenogram includes a first image of:
the object;
at least one reference marker having at least two fiducials, wherein the fiducials are separated by a fixed distance; and
the ring;
receiving, using the one or more processing devices and from the x-ray imager, a second roentgenogram of the object disposed between the x-ray source and the x-ray imager in a second orientation, wherein the second roentgenogram is generated by the x-ray imager, wherein the second orientation comprises a second angular position of the object relative to the imaging axis, wherein the second roentgenogram includes a second image of:
the object;
the at least one reference marker; and
the ring;
determining, using the one or more processing devices, a first 3-D position of the x-ray source with respect to the x-ray imager in the first orientation using the first image of the at least one reference marker;
determining, using the one or more processing devices, a second 3-D position of the x-ray source with respect to the x-ray imager in the second orientation using the second image of the at least one reference marker;
receiving, using the one or more processing devices, a first ring outline of the imaged ring in the first roentgenogram;
generating, using the one or more processing devices, a first 3-D ring projection from the first ring outline in the first roentgenogram to the first 3-D position of the x-ray source;
determining, using the one or more processing devices, a first ring position from the x-ray imager in the first orientation using the first 3-D ring projection and the fixed diameter of the ring;
receiving, using the one or more processing devices, a second ring outline of the imaged ring in the second roentgenogram;
generating, using the one or more processing devices, a second 3-D ring projection from the second ring outline in the second roentgenogram to the second 3-D position of the x-ray source;
determining, using the one or more processing devices, a second ring position from the x-ray imager in the second orientation using the second 3-D ring projection and the fixed diameter of the ring;
determining, using the one or more processing devices, the 3-D position of the ring with respect to the x-ray imager in the first and second orientations using the first and second ring outlines and the first and second ring positions;
identifying, using the one or more processing devices, a first object outline of the imaged object in the first roentgenogram;
generating, using the one or more processing devices, a first 3-D object projection from the first outline of the imaged object to the first 3-D position of the x-ray source;
identifying, using the one or more processing devices, a second object outline of the imaged object in the second roentgenogram;
generating, using the one or more processing devices, a second 3-D object projection from the second outline of the imaged object to the second 3-D position of the x-ray source;
aligning, using the one or more processing devices, the first and second 3-D object projections in a 3-D reference frame using the 3-D positions of the ring with respect to the x-ray imager in the first and second orientations; and
transforming, using the one or more processing devices, the first and second 3-D object projections into a 3-D model of the imaged object in the 3-D reference frame.

35. The method according to claim 34, the method further comprising:
identifying, using the one or more processing devices, a tilt axis in the 3-D reference frame, wherein the tilt axis passes between a first 3-D position in the 3-D reference frame that corresponds to the first position of the x-ray source in the first orientation and a second 3-D position in the 3-D reference frame that corresponds to the second position of the x-ray source in the second orientation;
identifying, using the one or more processing devices, one or more intersection planes passing through the tilt axis and through the first and second 3-D projections of the imaged object in the 3-D reference frame;
for each of the one or more intersection planes, performing the following steps a) through c):
a) identifying, using the one or more processing devices, one or more intersection points between the first and second 3-D object projections, and said intersection plane in the 3-D reference frame;
b) generating, using the one or more processing devices, one or more polygons connecting the intersection points in said intersection plane;
c) generating, using the one or more processing devices, one or more closed curves within the each of the one or more polygons, wherein the one or more closed curves corresponds to a cross-sectional view of the imaged object in said intersection plane; and
generating, using the one or more processing devices, a surface in the 3-D reference frame that connects each of the closed curves to form a 3-D model of the imaged object.

36. The method according to claim 34, wherein the ring comprises a plurality of object markers being attached thereto, wherein the plurality of object markers each include at least one fiducial, and wherein:

receiving, using the one or more processing devices, the first ring outline comprises receiving an outline of the fiducial of each object marker in the first roentgenogram;

generating, using the one or more processing devices, the first 3-D ring projection comprises generating a projection of the fiducial of each object marker from the first ring outline in the first roentgenogram to the first 3-D position of the x-ray source;

determining, using the one or more processing devices, the first ring position comprises determining a first ring center location from the x-ray imager in the first orientation using the first 3-D ring projection and the fixed diameter of the ring;

receiving the second ring outline comprises receiving an outline of the fiducial of each object marker in the second roentgenogram;

generating, using the one or more processing devices, the second 3-D ring projection comprises generating a projection of the fiducial of each object marker from the second ring outline in the second roentgenogram to the second 3-D position of the x-ray source;

determining, using the one or more processing devices, the second ring position comprises determining a second ring center location from the x-ray imager in the second orientation using the second 3-D ring projection and the fixed diameter of the ring; and determining, using the one or more processing devices, the 3-D position of the ring with respect to the x-ray imager in the first and second orientations comprises aligning the first and second ring center locations.

37. The method according to claim 36, wherein the plurality of object markers are disposed diametrically on the ring.

38. The method according to claim 36, wherein the at least one object marker is made of a radio-translucent material and the fiducial of the at least one object marker is made of a radio-opaque material.

39. The method according to claim 34, wherein the at least one reference marker comprises at least three fiducials in total, the method further comprising:

receiving, using the one or more processing devices, a first outline of the at least three fiducials in the first roentgenogram; and receiving, using the one or more processing devices, a second outline of the at least three fiducials in the second roentgenogram;

wherein determining the first 3-D position of the x-ray source comprises identifying a first plurality of paths from the x-ray source to the first outline of the least three fiducials and determining an approximate intersection of the first plurality of paths; and wherein determining the second 3-D position of the x-ray source comprises identifying a second plurality of paths from the x-ray source to the first outline of the least three fiducials and determining an approximate intersection of the second plurality of paths.

40. The method according to claim 39, wherein determining the approximate intersection of the first plurality of paths and the approximate intersection of the second plurality of paths comprises using an approximation model.

41. The method according to claim 34, wherein the at least one reference marker is made of a radio-translucent material and the fiducials of the at least one reference marker are made of a radio-opaque material.

* * * * *